United States Patent [19]

Berlin et al.

[11] Patent Number: 4,910,311

[45] Date of Patent: Mar. 20, 1990

[54] 3-7-DIHETERABICYCLO[3.3.1]NONANES AS ANTIARRHYTHMIC AGENTS

[75] Inventors: Kenneth D. Berlin; Mark D. Thompson, both of Stillwater; Benjamin J. Scherlag, Oklahoma City; Gary S. Smith, Stillwater, all of Okla.

[73] Assignee: Board of Regents for the Oklahoma Agricultural Mechanical Colleges, acting for and on behalf of Oklahoma State Univ., Stillwater, Okla.

[21] Appl. No.: 222,057

[22] Filed: Jul. 8, 1988

Related U.S. Application Data

[62] Division of Ser. No. 48,325, May 11, 1987, Pat. No. 4,778,892.

[51] Int. Cl.$^4$ .............................................. C07D 517/08
[52] U.S. Cl. ................................................... 546/122
[58] Field of Search ......................................... 546/122

[56] References Cited

PUBLICATIONS

Thompson et al., J. Med. Chem., vol. 30(5), pp. 780–788 (1987); Chem. Abst., vol. 106, 156448 (1987).

*Primary Examiner*—Mary C. Lee
*Assistant Examiner*—Bernard I. Dentz
*Attorney, Agent, or Firm*—Head & Johnson

[57] ABSTRACT

3-7,Diheterabicylo[3.3.1]nonanes and derivatives thereof are disclosed. Their method of preparation and use as antiarrhythmic agents is given.

18 Claims, No Drawings

3-7-DIHETERABICYCLO[3.3.1]NONANES AS ANTIARRHYTHMIC AGENTS

This is a divisional of co-pending application Ser. No. 07/048,325 filed on May 11, 1987 now U.S. Pat. No. 4,778,892.

BACKGROUND OF THE INVENTION

1. Field of the Invention:

This invention relates to antiarrhythmic compositions. More specifically, the invention relates to certain 3-7-diheterabicyclo[3.3.1]nonanes and derivatives thereof.

2. Description of the Prior Art:

3-azabicyclo[3.3.1]nonanes, including bicyclic systems with one heteroatom such as N, S and O and various derivatives, are known and are documented in the chemical literature. In a Chemical Reviews article, 1981, Vol. 81, No. 2, pages 149–174, entitled "Chemistry of 3-Azabicyclo[3.3.1]nonanes" by R. Jeyaraman and S. Avila the synthesis, stereochemistry, and reactions of such compounds are reviewed. This article acknowledges the close resemblence of aza- and diazaadamantanes in conformation and stereochemistry to the 3-azabicyclo[3.3.1]nonanes as a cause for significant progess in the azabicyclononane (ABN) studies. The article further acknowledges the ease of formation of 3-ABNs from simple ketones and aldehydes through the Mannich reaction without the involvement of complicated reaction conditions and reagents and the ready availability of a reactive carbonyl group in most of the ABNs prepared as important reasons for widespread studies on ABNs.

According to the existing chemical literature, some derivatives of 3-ABN have been found to possess useful biological activities. The observed biological activies have included potent analgesic properties and antitusive activities as well as antagonism to analgesic effects and even weak narcotic antagonism depending on the particular compound involved. Some have displayed local anesthetic activity and simple 3-ABN is reportedly effective against influenza infection. Other derivatives of 3-ABN have displayed powerful gangioplegic and hypotensive properties. Several have been found to be sedatives, antipyretics, and psycholaleptic and hypoglycemic agents. Some 3,7-diazabicyclo[3.3.1]nonanes possess antiarrhythmic potencies.

The Chemical Reviews article further described the subclass of 3-thia-7-azabicyclo[3.3.1]nonanes as being of much less interest and identifies a series of diphenyl and/or diaryl substituted derivatives as having been prepared through the Mannich reaction. In U.S. Pat. No. 4,581,361 certain 3-thia-7-azabicyclo[3.3.1]nonanes and derivatives are disclosed and claimed as antiarrhythmic compounds.

SUMMARY OF THE INVENTION

The present invention involves novel 3,7-diheterabicyclo[3.3.1]nonanes containing more than one heteroatom such as Se, N, S and O. In particular the invention involves novel 3-selena-7-azabicyclo[3.3.1-]nonanes, corresponding nitrogen compounds, related polyheterotricyclo compounds and derivatives thereof. Thus the present invention provides novel 3-selena-7-azabicyclo[3.3.1]nonane-9-one compounds having the formula:

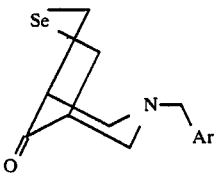

(1)

where Ar is:

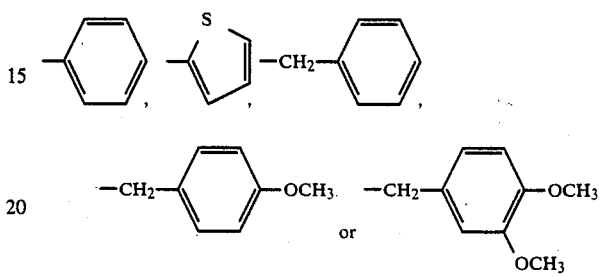

The present invention also provides novel 3-selena-7-azabicyclo[3.3.1]nonane compounds having the formula:

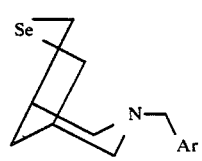

(2)

where Ar is:

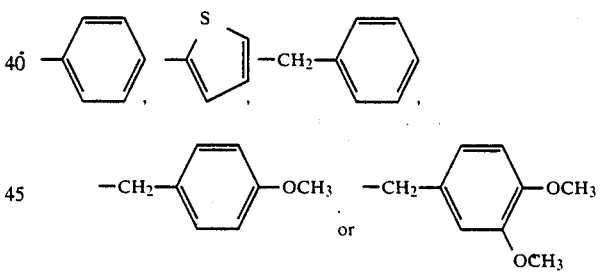

The invention further provides the hydroperchlorate, HCl, HBr and HI salts of the novel nonane compounds (2) and correspond salts of the 9-diol and 9-dimethoxy derivatives of the selena nonanes and methyl phenylamine nonanes characterized by the formula:

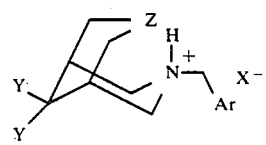

(3)

where Ar is:

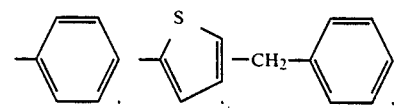

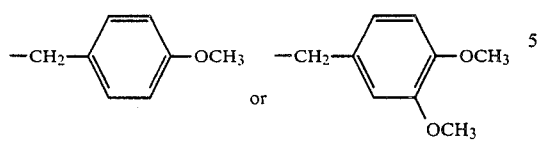

Z is Se, S or

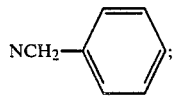

Y=—H, —OH or —OCH₃ and X is ClO₄⁻, Cl⁻, Br⁻or I⁻.

In a similar manner the invention provides the 6,8-diaryl substituted, selenium and nitrogen 3,7-diheterabicyclo[3.3.1]nonanes including the 9-one, 9-diol and 9-dimethoxy derivatives as well as the corresponding acid salts characterized by the formulae:

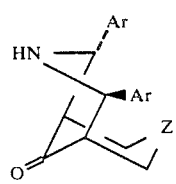 (4)

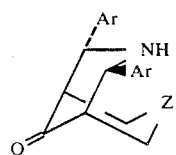 (5)

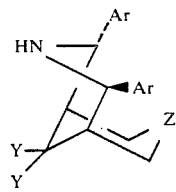 (6)

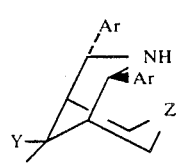 (7)

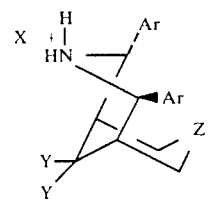 (8)

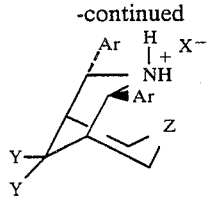 (9)

where Ar is Ph (i.e.,

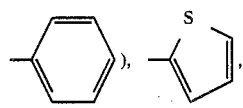

CH₂Ph,p-H₃C₆H₄CH₂, 3,4-(H₃CO)₂C₆H₂CH₂, o-ClC₆H₄, or p-ClC₆H₄; X⁻is ClO₄⁻, Cl⁻, Br⁻, or I⁻; Z is Se, S, O, or NCH₂Ph; and Y is H, OH, or OCH₃.

The invention still further provides for related polyheterotricyclo compounds and corresponding derivatives thereof characterized by the formulae:

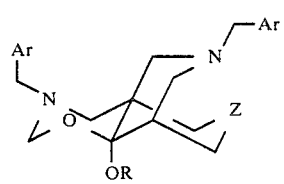 (10)

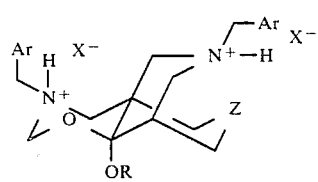 (11)

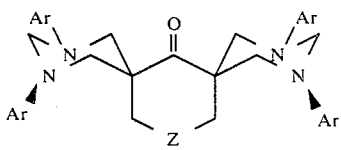 (12)

where Ar is Ph, CH₂Ph, o-H₃CC₆H₄, p-H₃CC₆H₄, o-H₃COC₆H₄,p-H₃COC₆H₄, o-ClC₆H₄, or p-ClC₆H₄; X⁻is ClO₄⁻, Cl⁻, Br⁻, or I⁻; Z is Se, S, O, CHR or NR'; R is CH₃, C₂H₅, n-C₃H₇or i-C₃H₇; and R' is H, CH₃, C₂H₅ or C(CH₃)₃.

More specifically the invention relates to the 3-selena-7-azabicyclo[3.3.1]nonane compounds and their respective hydroperchlorate salts as used in an antiarrhythmic process.

Thus, it is an object of the present invention to provide novel compositions that display biological activity. Fulfillment of this object and the presence and fulfillment of other objects will be apparent upon complete reading of the specification and claims.

DESCRIPTION OF THE PREFERRED EMBODIMENTS

The chemical compositions according to the preferred embodiments of the present invention are heteronuclear ring organic compounds based on the 3,7-diheterabicyclo[3.3.1]nonane structure as follows:

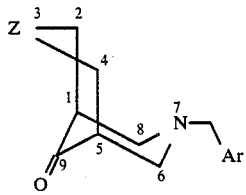 (13)

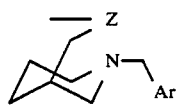 (14)

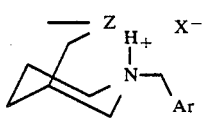 (15)

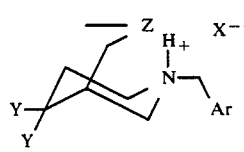 (16)

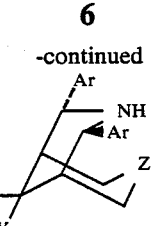 (7)

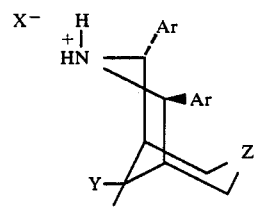 (8)

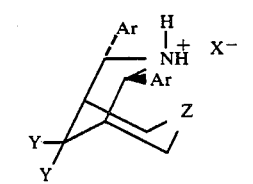 (9)

Wherein the 3-position of the 9-one structure for formula (13) is selenium, but includes oxygen, nitrogen as well as selenium in the other formulae (14), (15) and (16) and also sulfur in the 9-disubstituted of formula (16). The 7-position is an alkylated nitrogen atom (aryl substituted tertiary amine) and includes the acid amine salts such as the perchlorate and halogen acid salts, preferably the hydroperchlorate salt. The disubstituted 9-position of the formula (16) is preferably either a 9-diol or 9-dialkyloxy structure.

The novel chemical compositions according to the preferred embodiments of the present invention also include the 6,8-diaryl substituted 3,7-diheterabicyclo[3.3.1]nonane structures as follows:

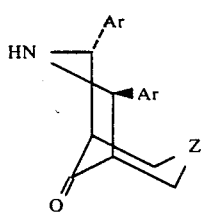 (4)

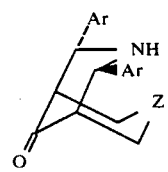 (5)

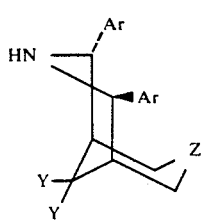 (6)

In these 6,8-diaryl substituted derivatives, the 3-position is preferably selenium, sulfur, nitrogen, oxygen and carbon and includes the endo-endo and endo-exo isomers. As in the previous formulae (13) through (16), the 9-position can be preferably unsubstituted, 9-one, 9-diol or 9,9-dimethoxy and also includes the alkylated nitrogen atom at the 7-position and their corresponding tertiary amine acid salts (hydroperchlorate, HCl, HBr and HI).

The novel chemical compositions according to the preferred embodiments of the present invention further includes the related polyheteratricyclo compounds based on the following structural formulae:

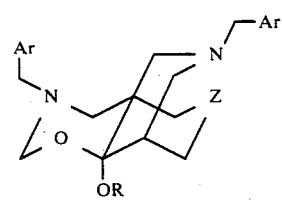 (10)

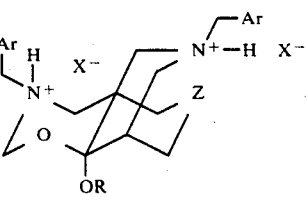 (11)

(12)

In these tricycle compounds, the hereto atoms include selenium, sulfur, oxygen and nitrogen along with either two or four alkylated nitrogen atoms as well as a tertiary amine acid salts (preferably the hydroperchlorate).

These compounds are the active ingredients for potential drugs and/or intermediates for the active ingredients of potential drugs for use in the treatment of disorders of the heart. They display good antiarrhythmic activity and as such are viable candidates to control arrhythmias in humans who have suffered heart attacks or infarctions.

Typically, the 9-one and the tricyclo ether oxygen and ketone containing compounds are synthesized by the reaction of a tetrahydroheterapyranone in the presents of an aldehyde and amine or ammonium salt according to a Mannich or Mannich-type reaction. For example, and as illustrated in the following reaction scheme A, 4-selenanone (17) is typically reacted with an amine such as benzylamine, 2-aminomethylthiophene, phenethylamine, p-methoxyphenethylamine, 3,4-dimethoxyphenethylamine and the like and paraformaldehyde in the presence of glacial acetic acid and methanol to produce the 3-selena-7-azabicyclo[3.3.1]nonane-9-ones (18). The 9-one (18) is then either reduced with hydrazine hydrate in triethylene glycol/potassium hydroxide media and then reacted directly with perchloric acid in benzene yielding the hydroperchlorate of 3-selena-7-azabicyclo[3.3.1]nonanes (19) or the corresponding 9,9-diol derivatives (20) respectively.

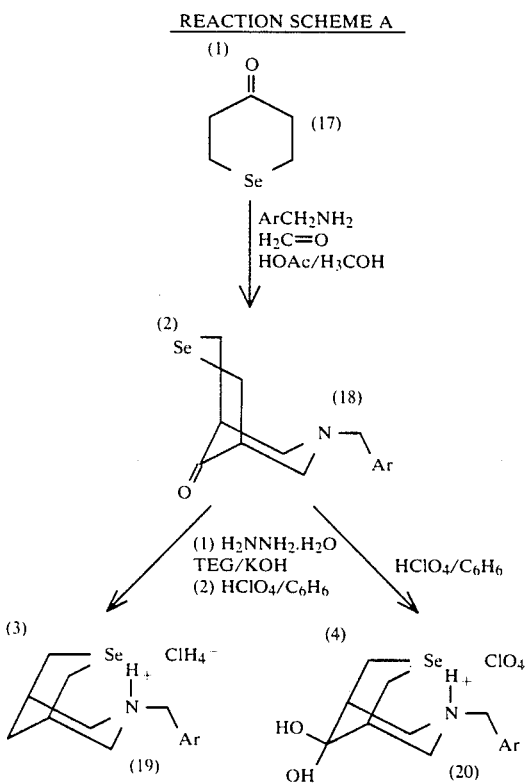

In reaction scheme B, the tetrahydroheterapyranone is reacted with an aldehyde in absolute ethanol and ammonium acetate to produce a mixture of 6,8-aryl substituted 3,7-diheterabicyclo[3.3.1]nonan-9-one isomers. As specifically illustrated in scheme B using 4-selenanone (17) as the reactant, a mixture of 6,8-diaryl-3-selena-7-azabicyclo[3.3.1]nonan-9-one isomers (21) and (22) are synthesized. As further illustrated and after isolation, the isomer is converted sequentially to the corresponding 6,8-diaryl-3-selena-7-azabicyclo[3.3.1-]nonane (23) using the reducing agent hydrazine hydrate followed by conversion to the secondary amine salt (24); i.e., hydroperchlorate in this embodiment.

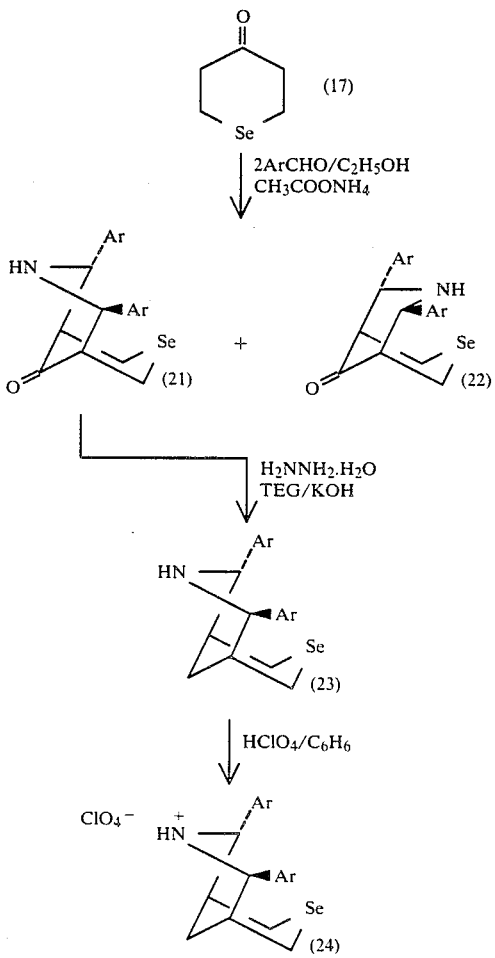

Reaction scheme C using 1-benzyl-4-piperidone (25) in a manner closely analogous to the previous reactions scheme A which used 4-selenanone as a reactant. As illustrated, the aryl amine (again benzylamine) and paraformaldehyde react in the presence of glacial acetic acid and methanol to produce the N,N'-dibenzyl-3,7-diazabicyclo[3.3.1]nonan-9-one (26). This diazabicyclo[3.3.1]nonan-9-one (26) is then converted to one of three derivatives by one of three separate reaction pathways. Using perchloric acid in benzene and 3Å molecular sieve with methanol, the hydroperchlorate amine salt of the 9,9-dimethoxy derivative (27) is produced. The use of perchloric acid in an aqueous media produces the hydraperchlorate amine salt of the 9,9-dihydroxy derivative (28). And, in a manner analogous to the reaction scheme A, a sequential reduction using hydrazine hydrate in triethylene glycol and potassium hydroxide followed by perchloric acid in benzene produces the hydroperchlorate tertiary amine salt of the reduced form of the diazabicyclo[3.3.1]nonane (29).

REACTION SCHEME C

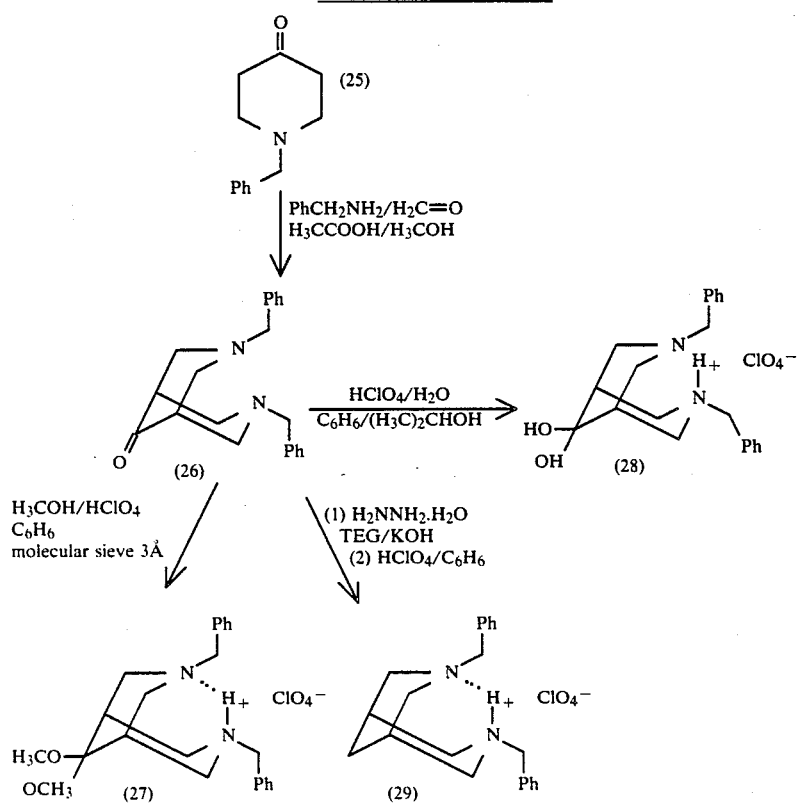

In reaction scheme D, the 1-benzyl-4-piperidone (25) of scheme C is reacted with an aromatic aldehyde (ortho-chlorobenzaldehyde in this specifically illustrated embodiment) with ammonium acetate and absolute ethanol in a manner similar to scheme B. An isomeric mixture of the 6,8-ortho-chlorobenzyl derivatives of 3,7-diazabicyclo[3.3.1]nonan-9-one (30) and (31) are produced. As further illustrated and with isomeric isolation, the 9-ones (30) and (31) are converted to the corresponding 6,8-bi(ortho-chlorophenyl) diazabicyclo[3.3.1]nonane (32) and (33) by the reducing agent hydrazine hydrate. This in turn can be converted to the isomeric mixture of the corresponding tertiary amine acid salts; i.e., hydroperchlorate salts in this illustrate (34) and (35).

REACTION SCHEME D

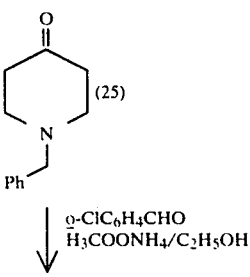

-continued
REACTION SCHEME D

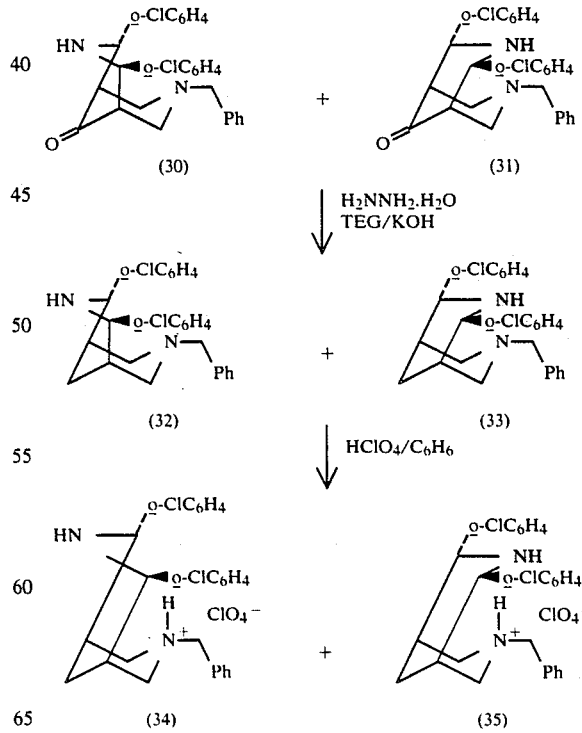

In the closely related reaction scheme E, the generic starting tetrahydroheterapyranone (36) is reacted with an amine (benzylamine as illustrated) and paraformaldehyde in glacial acetic acid and methanol. A resulting mixture of the dispiro[5.1.5.3]hexadecan-7-one (37) and the pyrido[3,4-e]-1,3-oxazine (38) are produced. As further suggested and after isolation the corresponding tertiary amine acid salts (the hydroperchlorate salt (39) in this illustrated embodiment) can be produced by the action of perchloric acid in benzene and isopropyl alcohol.

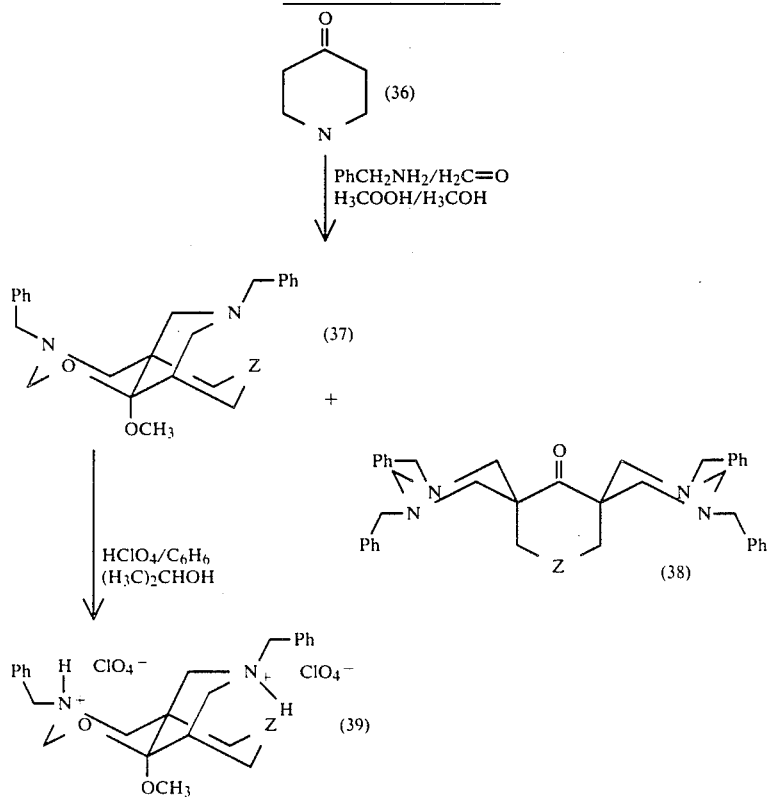

It should be appreciated that other tetrahydroheterapyranones, arylamines and aromatic aldehydes can readily be selected as reactants for the Mannich or Mannich-type reactions being illustrated in the reaction schemes. Similarly, various appropriate reactants can be employed in the selective oxidation or reduction at the 9-position as generally known in the art. The Mannich reaction is particularly useful in that, as previously indicated, it does not require complicated reaction conditions and reagents. However for purposes of the present invention, other methods of synthesis well known in the art should be considered equivalent. For example and for more detailed disclosure of various alternative methods of synthesis (including the Mannich reaction) and methods of synthesis of various subsequent derivatives, the previously mentioned Chemical Reviews article by Jeyaraman et al. is again cited and herein incorporated by reference for such purposes. Furthermore, according to the preferred embodiments of the present invention, the water solubility of the 3,7-hetrabicyclo[3.3.1]nonane compounds and related heteratricyclo compounds can be advantageously enhanced by formation of the corresponding tertiary amine salts and the like, prior to patient treatment.

In order to further illustrate the formation of the 3,7-diheterabicyclo[3.3.1]nonanes and related compounds according to the present invention, the preparation and isolation of purified, water soluble, biologically-active tertiary and secondary amine salts thereof and the antiarryhythmic activity of the compositions the following sequence of examples are presented.

EXAMPLE 1

7-Benzyl-3-selena-7-azabicyclo[3.3.1]nonan-9-one (40)

Benzylamine (0.67 g, 6.26 mmol) and glacial acetic acid (0.38 g, 6.33 mmol) were dissolved in dry methanol (30 mL). Paraformaldehyde (1.5 g, 50 mmol) was added and the resulting mixture was brought to reflux under an atmosphere of nitrogen. 4-Selenanone (1.00 g, 6.13 mmol) was then added in one portion which quickly turned the solution yellow. Boiling was continued under nitrogen in the dark for 5 hours. The resulting deep red solution was then allowed to cool to room temperature and was stirred for an additional 18 hours. The methanol was evaporated (aspirator) and the orange residual oil was partitioned between ether (50 mL) and water (50 mL). The ether layer was discarded and the aqueous layer was made basic with KOH (85%, 1.2 g 18.2 mmol). This solution was extracted with ether (5×40 mL). The combined extracts were dried ($K_2CO_3$) and evaporated (aspirator) to give an oil which was digested on a steam bath with Skelly B (50 mL). Evaporation gave a light yellow oil which solidified upon standing. This solid was recrystallized (95% ethanol) to give 7-benzyl-3-selena-7-azabicyclo[3.3.1-]nonan-9-one (0.78 g, 43%) as white needles: mp 91°–92° C.; IR (KBr) cm$^{-1}$ 1726 (C=O); $^1$H NMR (DCCl$_3$) δ2.71 [m, 4 H, H(1,5), H(6,8)ax], 3.08 [m, 2 H, H(6.8)], 3.20 [m, 4 H, H(2,4)], 3.57 [s, 2 H, H(11-

ArCH$_2$)], 7.32 [m, 5 H, ArH]; $^{13}$C NMR (DCCl$_3$) ppm 25.5 [t, C(2,4)], 46.2 [d, C(1,5)], 59.0 [t, C(6,8)], 61.5[t, C(11-ArCH$_2$)], 127.1 [d, C(4')], 128.2 (d) and 128.6 (d) [C(2',3',5',6')], 138.0 [s, C(1')], 213.8 [s, C(9)]; $^{15}$N NMR (DCCl$_3$) ppm 38.31 [N(7)]; $^{77}$Se NMR (DCCl$_3$) ppm 84.68 [Se(3)]. A satisfactory elemental analysis proved very difficult for the compound and thus it was converted to the hydroperchlorate salt without further purification.

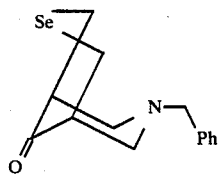

(40)

EXAMPLE II

7-(2-Thiophene)methyl-3-selena-7-azabicyclo[3.3.1]nonan-9-one (41)

A solution was made of 2-aminomethylthiophene (1.39 g, 12.3 mmol) and glacial acetic acid (1.10 g, 18.3 mmol) in methanol (60 mL) in a 150 mL, three-necked, round-bottomed flask equipped with a water-cooled condenser. To this solution was added paraformaldehyde (3.0 g, 100 mmol) and the resulting mixture was heated to reflux. 4-Selenanone (2.00 g, 12.3 mmol) was added and reflux was continued for 5 hours. After allowing the resulting red solution to cool to room temperature, the methanol was evaporated (aspirator) to give a red oil. This oil was partitioned between water and ether (100 mL:30 mL). The ether portion was discarded and the aqueous layer was made basic by the addition of NaOH (1.5 g, 37.5 mmol). The resulting yellow suspension was extracted with ether (5×40 mL). The combined extracts were washed with water (2×30 mL) and dried (K$_2$CO$_3$). Evaporation of the ether gave a brown oil which was digested in boiling Skelly B (3×100 mL). Evaporation of the Skelly B gave 1.72 g of 7-benzyl-3-selena-7-azabicyclo[3.3.1]nonan-9-one as a colorless viscous oil (47%): IR (film) cm$^{-1}$ 1710 (C=O); $^1$H NMR (CDCl$_3$) δ2.60–2.74 [m, 4 H, H(2,4)], 3.02–3.18 [m, 4 H, H(1,5), H(6,8)$_{ax}$], 3.27 [dd, 2 H, H(6,8)$_{eq}$, J=11.7 Hz, 3.4 Hz], 3.75 [s, 2 H, H(10)], 6.0–7.30 [m, 3 H, ArH]; $^{13}$C NMR (CDCl$_3$) ppm 24.8 [C(2,4)], 46.0 [C(1,5)], 55.6 [C(10)], 58.5 [C(6,8)], 124.9 [C(4')], 125.5 [C(2')], 126.1 [C(3')], 141.4 [C(1')], 212.9 [C(9)]; $^{15}$N NMR (CDCl$_3$) ppm 40.31 [N(7)]; $^{77}$Se NMR (CDCl$_3$) ppm 86.28 [Se(3)]. The compound was used without further purification.

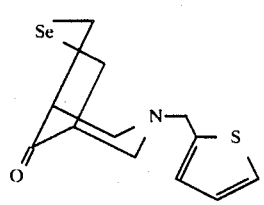

(41)

EXAMPLE III

7-Phenethyl-3-selena-7-azabicyclo[3.3.1]nonan-9-one (42)

A solution was made of phenethylamine (1.48 g, 12.3 mmol) and glacial acetic acid (0.85 g, 14.2 mmol) in methanol (60 mL). Paraformaldehyde (3.0 g, 100 mmol) was added and the resulting mixture was heated to reflux with magnetic stirring under an atmosphere of nitrogen. 4-Selenanone (2.00 g, 12.3 mmol) was added and boiling was continued for 5 hours resulting in an orange solution. Methanol was evaporated (aspirator) and the residual orange oil was mixed with water (200 mL). This aqueous mixture was made basic by addition of NaOH (2.0 g, 50 mmol) and was then extracted with ether (5×40 mL). The combined extracts were washed with saturated brine and dried (K$_2$CO$_3$). Evaporation (aspirator) gave a brown residue which was digested in boiling Skelly B (150 mL). Evaporation of Skelly B (150 mL). Evaporation of the Skelly B gave a solid which was recrystallized (ethanol) to give 0.82 g (22%) of 7-phenethyl-3-selena-7-azabicyclo[3.3.1]nonan-9-one as a light tan solid: mp 91°–92° C.; IR (KBr) cm$^{-1}$ 1710 (C=O); $^1$H NMR (DCCl$_3$ δ2.62–283 [m, 8 H, H(2,4,1,5,10-ArCH$_2$)], 3.02–3.20 [m, 6 H, H(6,8,11-NCH$_2$)], 7.16–7.38 [m, 5 H, Ar-H]; $^{13}$C NMR (DCCl$_3$) ppm 25.4 [5, C(2,4)], 33.7 [5, C(10-ArCH$_2$)], 46.2 [d, C(1,5)], 58.3 [5, C(11-NCH$_2$)], 59.1 [t, C(6,8)], 125.9 [s, C(4')], 128.1 [d, C(2',6') or C(3',5')], 128.4 [d, C(3',5') or C(2',6')], 139.7 [s, C(1')], 213.5 [s, C(9)]; $^{15}$N NMR (DCCl$_3$) ppm 35.44 [N(7)]; $^{77}$Se NMR (DCCl$_3$) ppm 79.51 [Se(3)]. The compound was converted to the hydroperchlorate salt without further purification.

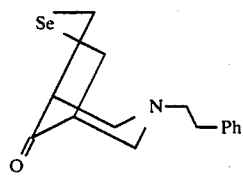

(42)

EXAMPLE IV

7-p-Methoxyphenethyl-3-selena-7-azabicyclo[3.3.1]nonan-9-one (43)

A solution was made of p-methoxyphenethylamine (0.93 g, 6.16 mmol) and glacial acetic acid (0.50 g, 8.33 mmol) in methanol (40 mL). Paraformaldehyde (1.50 g, 50.0 mmol) was added and the resulting mixture was heated to reflux under an atmosphere of nitrogen. 4-Selenanone 10 (1.00 g, 613 mmol) was added in one portion and boiling was continued for 4 hours. The methanol was evaporated (aspirator) from the resulting orange solution to give a very viscous red oil. This oil was dissolved in water (150 mL) and KOH (85%, 1.0 g, 15.2 mmol) was added to make the solution very basic. The resulting yellow suspension was extracted with ether (5×40 mL). The combined extracts were washed with water 930 mL) and dried (K$_2$CO$_3$). Evaporation of the ether (aspirator) gave 0.72 g (35%) 7-p-methoxyphenethyl-3-selena-7-azabicyclo[3.3.1]nonan-9-one as a light yellow oil: IR (neat) cm$^{-1}$ 1723 (C=O); $^1$H NMR (DCCl$_3$) δ2.50–2.80 [m, 8 H, H(1,5,2,4,10-ArCH$_2$)], 2.96–3.14 [m, 6 H, H(6,8,11,NCH$_2$)], 3.71 [s, 3 H, OCH$_3$], 6.72–6.90 [m, 2 H, H(3',5')], 7.00–7.16 [m, 2 H, H(2',6')]; $^{13}$C NMR (DCCl$_3$) ppm 24.6 [C(2,4)], 32.0 [C(10-ArCH$_2$)], 45.4 [C(1,5)], 54.2 [OCH$_3$], 57.8 [C(11-NCH$_2$)], 58.2 [C(6,8)], 112.8 [C(3',5')], 128.5 [C(2',6')], 130.9 [C(1')], 156.9 [C(4')], 212.5 [C(9)]; $^{15}$N NMR (DCCl$_3$) ppm 35.43 [N(7)]; $^{77}$Se NMR (DCCl$_3$) [Se(3)] ppm 78.81. Without further purification the compound was converted to the hydroperchlorate salt.

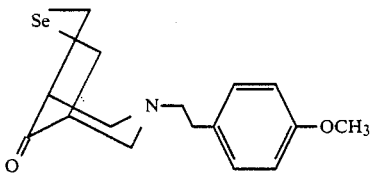

(43)

EXAMPLE V

7-(3,4-Dimethoxy)phenethyl-3-selena-7-azabicyclo[3.3.1]nonan-9-one (44)

A solution was made of 3,4-dimethoxyphenethylamine (2.23 g, 12.3 mmol) and glacial acetic acid (1.0 g, 16.6 mmol) in methanol (60 mL). Paraformaldehyde (3.0 g, 100 mmol) was added and the resulting mixture was heated to boiling. 4-Selenanone (2.00 g, 12.3 mmol) was added and boiling was continued for 4 hours. The resulting brown solution was evaporated (aspirator) to a brown oil. This oil was added to water (150 mL) and the mixture which formed was extracted with ether (4×50 mL). The combined extracts were washed with water (30 mL) and dried (K$_2$CO$_3$). Evaporation (aspirator) gave a dark brown oil which was digested in boiling Skelly B (3×100 mL). After decantation from a small amount of residual oil, evaporation of the supernatant gave 1.4 g of 7-(3,4-dimethoxy)phenethyl-3-selena-7-azabicyclo[3.3.1]nonan-9-one as a pale yellow viscous oil (31%): IR (neat) cm$^{-1}$ 1730 (C=O); $^1$H NMR (DCCl$_3$) δ2.60–2.80 [m, 8 H, H(2,4,1,5,10-ArCH$_2$)], 3.00–3.20 [m, 6 H, H(6,8,11-NCH$_2$)], 3.80 [s, 3 H, OCH$_3$], 3.84 [s, 3 H, OCH$_3$], 7.70–7.90 [m, 3 H, ArH]; $^{13}$C NMR (DCCl$_3$) ppm 25.4 [C(2,4)], 33.2 [C(10-ArCH$_2$)], 46.2 [C(1,5)], 55.7 [both OCH$_3$], 58.6 [C(11-NCH$_2$)], 59.1 [C(6,8)], 111.3, 112.0, 120.5, 132.8 [C(1')], 141.2, 148.7, 213.8 [C(9)]; $^{15}$N NMR (DCCl$_3$) ppm 35.16 [N(7)); $^{77}$Se NMR (DCCl$_3$) ppm 77.00 [Se(3)]. Without further purification, the compound was converted to the hydroperchlorate salt.

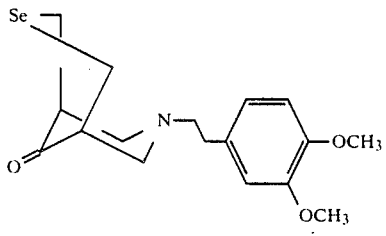

(44)

EXAMPLE VI

7-Benzyl-3-selena-7-azabicyclo[3.3.1]nonane Hydroperchlorate (45)

A solution was made of 7-benzyl-3-selena-7-azabicyclo[3.3.1]nonan-9-one (2.0 g, 6.8 mmol) and hydrazine (95%, 5.0 g, 148 mmol) in triethylene glycol (40 mL). Potassium hydroxide (85%, 10.0 g, 152 mmol) was added and the resulting mixture was heated to 140° C. in an oil bath under a nitrogen atmosphere for 12 hours. After cooling to room temperature, the solution was poured into water (200 mL) and the resulting suspension was extracted with ether (5×40 mL). The combined extracts were dried overnight (K$_2$CO$_3$) and cooled to 0° C. Perchloric acid (60%, 2.0 g, 11.9 mmol) was added dropwise. The yellow orange solid which formed was filtered and recrystallized (methanol) to give 7-benzyl-3-selena-7-azabicyclo[3.3.1]nonane hydroperchlorate (1.94 g, 75%) as white needles: mp 161.0°–162.0° C. (dec); IR (KBr) cm$^{-1}$ 3440, 1105; $^1$H NMR (DMSOd$_6$) δ1.75 [d, 1 H, H(9), J=13.7 Hz], 1.88 [d, 1 H, H(9), J=13.6 Hz], 2.41 [br s, 2 H, H(1,5)], 2.64 [d, 2H, H(2,4)$_{ax}$, J=12.21 Hz], 3.19 [d, 2 H, H(2,4)$_{eq}$, J=12.10 Hz], 3.42 [m, 2 H, H(6,8)$_{ax}$], 3.61 [d, 2H, H(6,8)$_{eq}$, J=11.83 Hz], 4.32 [d, 2 H, H(10-NCH$_2$), J=5.75 Hz]; $^{13}$C NMR (DMSO-d$_6$) ppm 22.0 [C(2,4)], 25.2 [C(1,5)], 28.5 [C(9)], 56.6 [C(6,8)], 60.5 [C(10-NCH$_2$)], 128.9, 129.3, 129.8, 130.0 [ArC]; $^{15}$N NMR (DMSO-d$_6$) ppm 51.56 [N(7)]; $^{77}$Se NMR (DMSO-d$_6$) ppm 96.61 [Se(3)]. Analysis calculated for C$_{14}$H$_{20}$ClNO$_4$Se: C, 44.14; H, 5.30; N, 3.68; Cl, 9.32; Se, 20.75. Found: C, 44.45; H, 5.38; N, 3.61; Cl, 9.52; Se, 20.67.

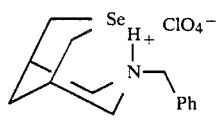

(45)

EXAMPLE VII

7-(2-Thiophene)methyl-3-selena-7-azabicyclo[3.3.1]nonane Hydroperchlorate (46)

7-(2-Thiophene)methyl-3-selena-7-azabicyclo[3.3.1]nonane hydroperchlorate (1.0 g, 3.33 mmol) and anhydrous hydrazine (95%, 2.0 g, 5.94 mmol) were dissolved in triethylene glycol (40 mL) in a 60 mL, jacketed flask which was equipped for distillation. Potassium hydroxide (85%, 3.0 g, 45.5 mmol) was added and the resulting mixture was heated with stirring to 140°–145° C. by boiling xylene in the jacket of the reaction vessel. Heating was continued for 4 hours after which time the reaction mixture was cooled to room temperature and was poured into cool water (150 mL). The resulting suspension was extracted with ether (5×40 mL) and the combined extracts were dried (K$_2$CO$_3$). After filtration of the desiccant, 60% HClO$_4$ (1.0 g, 6.0 mmol) was added dropwise, very slowly, causing an orange solid to form. The ether was decanted and the solid was recrystallized twice (isopropyl alcohol, decolorizing carbon) to give 0.88 g of 7-(2-Thiophene)methyl-3-selena-7-azabicyclo[3.3.1]nonane hydroperchlorate as white needles (68%): mp 141.0°–141.5° C.: IR (KBr) cm$^{-1}$ 3450, 1150; $^1$H NMR (DMSO-d$_6$) δ1.74 [d, 1 H, H(9), J=13.6 Hz], 1.86 [d, 1 H, H(9), J=13.6 Hz], 2.43 [br s, 2 H, H(1,5)], 2.64 [d, 2 H, H(2,4)$_{ax}$, J=12.0 Hz], 3.19 [d, 2 H, H(2,4)$_{eq}$, J=11.3 Hz], 3.35 [m, 2 H, H(6,8)$_{ax}$], 3.62 [d, 2 H, H(6,8)$_{eq}$, J=12.7 Hz], 4.53 [d, 12 H, H(10-NCH$_2$), J=5.3 Hz], 7.16 [dd, 1 H, H(3'), J=5.1 Hz, 3.7 Hz], 7.36 [d, 1 H, H(2'), J=3.3 Hz], 7.75 [d, 1 H, H(4'), J=5.1 Hz], 9.24 [br s, 1 H, H(7)]; $^{13}$C NMR (DMSO-d$_6$) ppm 21.9 [t, C(2,4)], 25.3 [d, C(1,5)], 28.6 [t, C(9)], 60.5 [t, C(10-NCH$_2$)], 56.2 [t, C(6,8)], 127.2 [d, C(4')], 129.3 [d, C(2')], 130.5 [s, C(1')], 131.8 [d, C(3')]; $^{15}$N NMR (DMSO-d$_6$) ppm 58.54 [N(7)]; $^{77}$Se NMR (DMSO-d$_6$)

ppm 89.41 [Se(3)]. Analysis calculated for $C_{12}H_{18}ClNO_4Se$: C, 37.27; H, 4.69; N, 3.62; Se, 20.42. Found: C, 37.30; H, 4.76; N, 3.60; Se, 20.10.

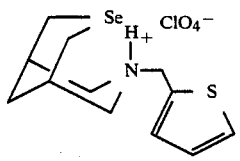
(46)

EXAMPLE VIII

7-Phenethyl-3-selena-7-azabicyclo[3.3.1]nonane Hydroperchlorate (47)

A jacketed flask was charged with a mixture of 7-phenethyl-3-selena-7-azabicyclo[3.3.1]nonan-9-one (1.3 g, 4.2 mmol) $N_2H_4$ (95%, 2.0 g, 59 mmol), and KOH (85%, 6.0 g, 91 mmol) in triethylene glycol (40 mL). The flask was equipped for simple distillation under a rapid stream of nitrogen. The reaction mixture was heated to 140°–145° C. by boiling xylene contained in the jacket. Heating was continued under a nitrogen stream for 5 hours. During this time, a small amount of water and hydrazine distilled out. The resulting clear, light brown solution was cooled in a water bath to room temperature and was then poured into ice-water (200 mL). The white suspension which formed was extracted with ether (5×40 mL). The combined ether extracts were washed with brine (30 mL) and dried ($K_2CO_3$) overnight. After filtering out the desiccant, this ether solution was cooled to 0°–5° C. in an ice bath and 60% $HClO_4$ (1.0 g, 6.0 mmol) was added dropwise, very slowly. After stirring overnight, the resulting orange precipitate was filtered and recrystallized (methanol, decolorizing carbon) to give 0.67 g (40%) of 7-phenethyl-3-selena-7-azabicyclo[3.3.1]nonane hydroperchlorate as white plates: mp 249°–250° C. (dec): IR (KBr) cm$^{-1}$ 3400, 1140; $^1$H NMR (DMSO-$d_6$) δ1.73 [br d, 1 H, H(9), J=14.0 Hz], 1.89 [br d, 1 H, H(9), J=13.8 Hz], 2.41 [br s, 2 H, H(1,5)], 2.64 [d, 2 H, H(2,4)$_{ax}$, J=12.1 Hz], 3.07 [t, 2 H, H(11-Ar$\underline{CH}_2$), J=7.9 Hz], 3.20 [d, 2 H, H(2,4)$_{eq}$, J=12.2 Hz], 3.33 [m, 4 H, H(10-N$\underline{CH}_2$), (6,8)$_{ax}$], 3.86 [d, 2 H, H(6,8)$_{eq}$, J=12.3 Hz], 7.28–7.50 [m, 5 H, Ar-H], 8.89 [br s, 1 H, H(7)]; $^{13}$C NMR (DMSO-$d_6$) ppm 21.9 [t, C(2,4)], 25.3 [d, C(1,5)], 28.5 [t, C(9) or C(11-Ar$\underline{CH}_2$)], 29.9 [t, C(11-Ar$\underline{CH}_2$) or C(9)], 56.7 [y, C(6,8)], 58.8 [t, C(10-N$\underline{CH}_2$)], 126.8 [d, C(4')], 128.5 [d, C(2',6',3',5')], 136.2 [s, C(1'))]; $^{15}$N NMR (DMSO-$d_6$) ppm 48.25 [N(7)]; $^{77}$Se NMR (DMSO-$d_6$) ppm 88.42 [Se(3)]. Analysis calculated for $C_{15}H_{22}ClNO_4Se$: C, 45.64; H, 5.62; N, 3.55; Se, 20.00. Found C, 45.77; H, 5.80; N, 3.48; Se, 19.85.

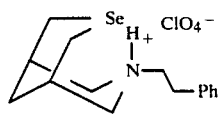
(47)

EXAMPLE IX

7-p-Methoxyphenethyl-3-selena-7-azabicyclo[3.3.1]nonane Hydroperchlorate (48)

A jacketed flask equipped for simple distillation was charged with a suspension of 7-p-methoxyphenethyl-3-selena-7-azabicyclo[3.3.1]nonan-9-one (0.65 g, 1.92 mmol), hydrazine (95%, 1.00 g, 29.7 mmol), and potassium hydroxide (85%, 3.0 g, 45.5 mmol) in triethylene glycol (25 mL). Under a rapid stream of nitrogen, the suspension was heated to 140°–145° C. by boiling xylene in the jacket of the flask. Stirring was continued at this temperature for 3 hours during which time a small amount of water and excess hydrazine distilled from the reaction mixture. After cooling to room temperature, the resulting solution was diluted with water (100 mL) and was extracted with ether (5×40 mL). The combined ether extracts were dried ($K_2CO_3$) overnight and 60% perchloric acid (0.5 g, 3.0 mmol) was added very slowly. This precipitated an orange solid. The ether was decanted and the solid was recrystallized (absolute ethanol) with the aid of decolorizing carbon to give 0.58 g (71%) of 7-p-methoxyphenethyl-3-selena-7-azabicyclo[3.3.1]nonane hydroperchlorate as white needles: mp 208.5°–209.0° C.; IR (KBr) cm$^{-1}$ 3425, 1085; $^1$H NMR (DMSO-$d_6$) δ1.73 [br d, 1 H, H(9), J=14 Hz], 1.90 [br d, 1 H, H(9), J=14 Hz], 2.42 [br s, 2 H, H(1,5)], 2.65 [d, 2 H, H(2,4)$_{ax}$, J=12 Hz], 3.02 [t, 2 H, H(11-Ar$\underline{CH}_2$) J=7 Hz], 3.22 [d, 2 H, H(2,4), J=14 Hz], 3.30 [m, 2$\overline{H}$, H(10-N$\underline{CH}_2$)], 3.36 [d, 2 H, H(6,8)$_{ax}$, J=12 Hz], 3.76 [s, 3 H, OC$\overline{H}_3$], 3.86 [d, 2 H, H(6,8)$_{eq}$, J=12 Hz], 6.97 [d, 2 H, H(3',5')], J=9 Hz], 7.32 [d, 2 H, H(2',6'), J=9 Hz], 8.92 [br s, 1 H, H(7)]; $^{13}$C NMR (DMSO-$d_6$) ppm 21.9 [t, C(2,4)], 25.3 [d, C(1,5)], 28.5 [t, C(9) or C(11)], 28.9 [t, C(11-Ar$\underline{CH}_2$) or C(9)], 55.0 [q, OC$\underline{H}_3$], 56.7 [t, C(6,8)], 58.9 [t, $\overline{C}$(10-N$\underline{CH}_2$)], 114.0 [d, C(3',5')], 127.7 [s, C(1')], 129.6 [d, C(2',6')], 158.1 [s, C(4')]; $^{15}$N NMR (DMSO-$d_6$) ppm 48.10 [N(7)]; $^{77}$Se NMR (DMSO-$d_6$) ppm 88.64 [Se(3)]. Analysis calculated for $C_{16}H_{24}ClNO_5Se$: C, 45.24; H, 5.69; N, 3.30; Se, 18.59. Found: C, 45.42; H, 5.80; N, 3.30; Se, 18.46.

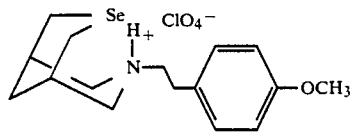
(48)

EXAMPLE X

7-(3,4-Dimethoxy)phenethy-3-selena-7-azabicyclo[3.3.1]nonane Hydroperchlorate (49)

A jacketed flask which was equipped for distillation, was charged with solution of 7-(3,4-dimethoxy)phenethyl-3-selena-7-azabicyclo[3.3.1]nonan-9-one (1.10 g, 3.00 mmol), anhydrous hydrazine (95%, 200 g, 5.94 mmol), and potassium hydroxide (85%, 3.0 g, 45.5 mmol) in triethylene glycol (40 mL). This solution was heated to 140°–145° C. by boiling xylene in the jacket of the reaction flask. Heating was continued for 4 hours during which time a small amount of water and excess hydrazine distilled. The reaction mixture, which had turned brown, was cooled and poured into cool water (150 mL). The resulting suspension was extracted with ether (4×50 mL). The combined extracts were washed with water (40 mL) and dried ($K_2CO_3$). Perchloric acid (60%, 1.0 g, 6.0 mmol) was added to the ether solution dropwise, very slowly. This precipitated a white solid which rapidly turned orange. The ether was decanted and the solid was recrystallized twice from absolute ethanol (decolorizing carbon) to give 0.92 g (68%) of 7-(3,4-dimethoxy)phenethy-3-selena-7-azabicyclo[3.3.1]nonane hydroperchlorate as a white crystalline solid: mp 162°–163° C.; IR (KBr) cm$^{-1}$ 3450, 1090, $^1$H NMR (DMSO-d$_6$) δ1.74 [d, 1H, H(9), J=13 Hz], 1.92 [d, 1 H, H(9), J=13 Hz], 2.42 [br s, 2 H, H(1,5)], 2.65 (d, 2 H, H(2,4)$_{ax}$, J=12 Hz], 3.02 [t, 2 H, H(11-ArCH$_2$)], 3.22 [d, 2 H, H(2,4)$_{eq}$, J=12 Hz], 3.36 [m, 4 H, H(10-NCH$_2$) and H(6,8)$_{ax}$], 3.76 [s, 3H, OCH$_3$], 3.80 [x, 3 H, OCH$_3$], 3.87 [d, 2 H, H(6,8)$_{eq}$, J=12 Hz], 6.88–7.02 [m, 3 H, ArH], 8.88 [br s, 1 H, H(7)]; $^{13}$C NMR (DMSO-d$_6$) ppm 22.0 [C(2,4)], 25.3 [C(1,5)], 28.5 [C(11) or C(9)], 29.4 [C(9) or C(11) ArCH$_2$)], 55.4 [OCH$_3$], 56.7 [C(6,8)], 58.9 [C(10)-NCH$_2$)], 112.0, 112.3, 120.6, 128.3 [C(1')], 147.7 [C(3') or C(4')], 148.8 [C(3') or C(4')]; $^{15}$N NMR (DMSO-d$_6$) ppm 48.03 [N(7)]; $^{77}$Se NMR (DMSO-d$_6$) ppm 88.35 [Se(3)]. Analysis calculated for C$_{17}$H$_{26}$ClNO$_6$Se: C, 44.90; H, 5.76; N, 3.08. Found: C, 44.86; H, 5.86; N, 3.04.

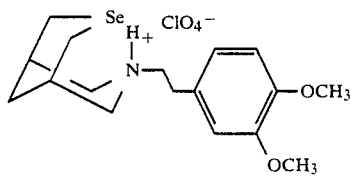

(49)

EXAMPLE XI

7-Benzyl-3-selena-7-azabicyclo[3.3.1]nonan-9,9-diol Hydroperchlorate (50)

7-Benzyl-3-selena-7-azabicyclo[3.3.1]nonan-9-one (0.65 g, 2.2 mmol) was dissolved in dry benzene (250 mL). Perchloric acid (60%, 1.0 g, 6.0 mmol) was added dropwise very slowly with cooling and swirling. This precipitated an orange solid which adhered to the side of the flask. The benzene was decanted and the solid was recrystallized (95% ethanol) to give 7-benzyl-3-selena-7-azabicyclo[3.3.1]nonan-9,9-diol hydroperchlorate (0.62 g, 68.3%) as white needles: mp 214.0°–216.0° C. (dec); IR (KBr) cm$^{-1}$ 3430, 1080; $^1$H NMR (DMSO-d$_6$) δ2.43 [br s, 2 H, H(2,4)$_{ax}$], 2.72 [br d, 2 H, H(2,4)$_{eq}$], 3.22–3.50 [m, 6 H, H(6,8)$_{ax}$, H(1,5), OH], 3.50–3.64 [m, 2 H, H(6,8)$_{eq}$], 4.35 [d, 2 H, H(10-NCH$_2$)], 7.40–7.70 [m, 5 H, ArH], 9.20 [br s, 1 H, H(7)]; $^{13}$C NMR (DMSO-d$_6$) ppm 21.1 [C(2,4)], 34.7 [C(1,5)], 54.9 [C(6,8)], 60.1 [C(10)-NCH$_2$)], 92.5 [C(9)], 129.2, 129.7, 130.0, 130.5 [ArC]; $^{15}$N NMR (DMSO-d$_6$) ppm 51.88 [N(7)]; $^{77}$Se NMR (DMSO-d$_6$) ppm 62.39 [Se(3)]. Analysis calculated for C$_{14}$H$_{20}$NClSeO$_6$: N, 3.39; Se, 19.13. Found: N, 3.20; Se, 19.51.

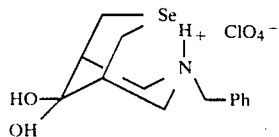

(50)

EXAMPLE XII 6,8-Diphenyl-3-selena-7-azabicyclo[3.3.1]nonan-9-one (51)

A jacketed flask was charged with a solution of dry ammonium acetate (2.31 g, 30.0 mmol) in absolute ethanol (30 mL) which was warmed to 65° C. by boiling methanol in the jacket. A solution of 4-selenanone (2.45 g, 15.0 mmol) and benzaldehyde (3.18 g, 30.0 mmol) in absolute ethanol (15 mL) was added in one portion. The resulting solution was stirred under nitrogen at 65° C. for 45 minutes. After cooling the reaction mixture to about 30°–40° C., ether (15 mL) was added and stirring was continued for 10 minutes. Cooling (5° C.) overnight resulted in the formation of a yellow solid which was filtered and recrystallized (ethanol) to give 0.89 g (17%) of 6,8-diphenyl-3-selena-7-azabicyclo[3.3.1]nonan-9-one as white needles: mp 207.0°–208.5° C. (dec); IR (KBr) cm$^{-1}$ 3320 (N—H), 1730 (C=O); $^1$N NMR (DCCl$_3$) δ1.77 [br s, 1 H, H(7)], 2.84 [br d, 4 H, H(2,4), J=8 Hz], 3.59 [m, 2 H, H(1,5)], 5.04 [m, 2 H, H(6,8)], 7.20–7.50 [m, 10 H,ArH]; $^{13}$C NMR (DCCl$_3$) ppm 92.2 [C(2,4)], 54.0 [C(1,5)], 64.2 [C(6,8)], 144.4 [C(1'), 127.0 [C(3',5') or C(2',6')], 127.9 [C(4')], 128.7 [C(2',6') or C(3',5)], 207.2 [C(9)]; $^{15}$N NMR (DCCl$_3$) ppm 63.28 [N(7)]; $^{77}$Se NMR (DCCl$_3$) ppm 25.38 [Se(3)]. Analysis calculated for C$_{19}$H$_{19}$NOSe: C, 64.04; H, 5.38; N, 3.93; Se, 22.17. Found: C, 63.86; H, 5.45; N, 3.81; Se, 21.90.

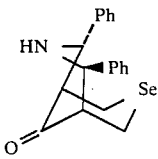

(51)

EXAMPLE XIII 6,8-Di(2-thiophene)-3-selena-7-azabicyclo[3.3.1]nonan-9-one (52)

A solution of 2-thiophenecarboxaldehyde (1.38 g, 12.3 mmol) and dry ammonium acetate (0.94 g, 12.3 mmol) in absolute ethanol (20 mL) was heated to boiling on a hot plate. To this was added a hot solution of freshly sublimed 4-selenanone 10 (1.00 g, 6.13 mmol) in absolute ethanol (15 mL). Boiling was continued for 10 minutes with ethanol being added to keep the volume constant. During this time the colorless solution turned yellow. The flask was removed from the hot plate, was stoppered, and was allowed to stand at room temperature for 3 days. The resulting dark red solution was decanted from the yellow solid which had formed during this time. The solid was taken up in benzene (100 mL) and was treated with decolorized carbon. Filtration followed by evaporation (aspirator) gave a light brown solid which was recrystallized (methanol) to give 0.40 g, (18%) of 6,8-Di(2-thiophene)-3-selena-7-azabicyclo[3.3.1]nonan-9-one as a light yellow solid: mp 155°–161° C. (dec); IR (KBr) cm$^{-1}$ 3260 (N—H), 1723 (C=O); $^1$H NMR (DCCl$_3$) δ2.16 [br s, 1 H, H(7)], 2.80 [m, 4 H, H(1,5) and H(2,4)$_{ax}$], 3.57 [d, 2 H, H(2,4)$_{eq}$, J=10.03 Hz], 5.32 [d, 2 H, H(6,8), J=3.96 Hz], 6.90–7.40 [m, 6 H, Ar-H]; $^{13}$C NMR (DCCl$_3$) ppm 29.3 [C(2,4)], 54.6 [C(1,5)], 59.1 [C(6,8)], 123.7, 124.8, 126.3 [C(2',3',4')], 147.0 [C(1')], 213.3 [C(9)]; $^{15}$N NMR (DCCl$_3$) ppm 67.09 [N(7)]; $^{77}$Se NMR (DCCl$_3$) ppm 30.60 [Se(3)].

6,8-Di(2-thiophene)-3-selena-7-azabicyclo[3.3.1]nonan-9-one proved difficult to purify in order to obtain a satisfactory elemental analysis. Thus it was used directly in the conversion to the amine 6,8-di(2-thiophene)-3-selena-7-azabicyclo[3.3.1]nonane of Example XVI which did lend itself to purification and was analyzed.

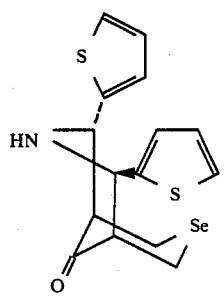

(52)

EXAMPLE XIV 6,8-Di(4-chlorophenyl)-3-selena-7-azabicyclo[3.3.1]nonan-9-one (the endo,exo isomer) (53),(54)

A solution of dry ammonium acetate (0.94 g, 12.3 mmol) and p-chlorobenzaldehyde (1.73 g, 12.3 mmol) in absolute ethanol (20 mL) was heated to boiling in a 50-mL, Erlenmeyer flask on a hot plate. To this solution was added a boiling solution of freshly sublimed 4-selenanone (1.00 g, 6.13 mmol) in absolute ethanol (15 mL). The combined solutions were boiled for 10 min with ethanol being added to keep the volume constant. During this time the colorless solution became light yellow. The flask was then removed from the hot plate and stoppered. The reaction mixture was allowed to stand at room temperature for 3 days, during which time the solution turned dark reddish-brown and a yellow solid formed. The liquid was decanted and the solid was dissolved in benzene (100 mL). This solution was treated with decolorizing carbon and was filtered. Evaporation (aspirator) of the benzene gave a light brown solid which was recrystallized (absolute ethanol) giving 0.33 g. (13%) of 6,8-di(4-chlorophenyl)-3-selena-7-azabicyclo[3.3.1]nonan-9-one (the endo,exo isomer) as a light tan solid: mp 219°–220° C. (dec); IR (KBr) cm$^{-1}$ 3280 (N—H), 1722 (C=O); $^1$H NMR (DCCl$_3$) δ1.70 [br s, 1 H, H(7)], 2.69 [m, 4 H, H(1,5) and H(2,4)$_{ax}$], 3.56 [d, 2 H, H(2,4)$_{eq}$, J=10.20 Hz], 4.99 [d, 2 H, H(6,8), J=4.07 Hz], 7.30–7.40 [m, 8 H, Ar-H]; $^{13}$C NMR (DCCl$_3$) ppm 29.0 [C(2,4)], 53.0 [C(1,50], 63.4[C(6,8)], 128.2 [C(2',6') or C(3',5')], 128.8 [C(3',5') or C(2',6')], 133.7 [C(4')], 142.5 [C(1')], 213.4 [C(9)]; $^{15}$N NMR (DCCl$_3$) ppm 62.84 [N(7)]; $^{77}$Se NMR (DCCl$_3$) ppm 26.67 [Se(3)].

6,8-Di(4-chlorophenyl)-3-selena-7-azabicyclo[3.3.1]nonan-9-one (the endo,exo isomer) proved very difficult to purify for elementary analysis. It was converted to amine 6,8-di(4-chorophenyl)-3-selena-7-azabicyclo[3.3.1]nonane.

Addition of water (10 mL) to the original mother liquor caused the precipitation of a dense brown solid. After allowing this mixture to stand at room temperature overnight, the solid was filtered and recrystallized (ethanol, decolorizing carbon) to give 0.2 g (7%) of 6,8-di(4-chlorophenyl)-3-selena-7-azabicyclo[3.3.1]nonan-9,-one (the endo, endo isomer) as a light tan solid: mp 168°–171° C. (dec); IR (KBr) cm$^{-1}$ 3315 (N—H), 1710 (C=O); $^1$H NMR (CDCl$_3$) δ2.68–2.90 [m, 2 H, H(2,4)$_{ax}$], 2.83 [br s, 2 H, H1,5)], 3.06–3.18 [m, 2 H, H(2,4)$_{eq}$], 4.48 [br s, 2 H, H(6,8)], 7.30–7.60 [m, 8 H, ArH]; $^{13}$C NMR (CDCl$_3$) ppm 20.9 [t, C(2,4)], 51.5 [d, C(1,5)], 63.8 [d, C(6,8)], 127.7 [d, C(2') or C(3')], 128.8 [d, C(3') or C(2')], 133.4 [s, C(4')], 137.6 [s, C(1')], 212.9 [s, C(9)]; $^{15}$N NMR (CDCl$_3$) ppm 44.24 [N(7)]; $^{77}$Se NMR (CDCl$_3$) ppm 122.66 [Se(3)].

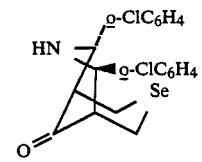

(53)

(54)

EXAMPLE XV 6,8-Diphenyl-3-selena-7-azabicyclo[3.3.1]nonane (55)

6,8-Diphenyl-3-selena-7-azabicyclo[3.3.1]nonan-9-one (0.89 g, 2.5 mmol) and hydrazine (95%, 3.0 g, 89 mmol) were dissolved in triethylene glycol (40 mL). This solution was placed in a jacketed flask equipped for simple distillation under a rapid stream of nitrogen. Water was boiled in the jacket which heated the reaction mixture to about 100° C. The solution was stirred at this temperature for 2 hours. Potassium hydroxide (85%, 1.0 g, 15 mmol) was added and the temperature was increased to about 208° C. by boiling tetralin in the jacket. As the temperature increased a gas evolved, presumably nitrogen. After stirring at this temperature for 4 h, 3 mL of water and excess hydrazine had distilled out. The reaction mixture was cooled to 60°–70° C. and was then poured into ice-water (200 mL). The filtered solid was recrystallized (ether, decolorized carbon) to give 0.63 g (74%) of amine 6,8-diphenyl-3-selena-7-azabicyclo[3.3.1]nonane as white needles: mp 193.5°–195.0° C. (dec); IR (KBr) cm$^{-1}$ 3250 (N—H); $^1$H NMR (C$_6$D$_6$) δ0.83 [dt, 1 H, H(9), J=12.0, 1.5 Hz], 1.34 [m, 1 H, H(7)], 1.78 [m, 2 H, H(1,5)], 2.00 [dd, 2 H, H(2,4)$_{ax}$, J=12.0, 1.4 Hz], 2.33 [m, 1 H, H(9)], 2.84 [dd, 2 H, H(2,4)$_{eq}$, J=12.0, 2.0 Hz], 4.34 [d, 2 H, H(6,8), J=2.0 Hz], 7.1–7.4 [m, 10 H, ArH]; $^{13}$C NMR (D$_6$D$_6$ @ 50° C.) ppm 25.1 [C(2,4)], 27.2 [C(9)], 34.5 [C(1,5)], 62.0 [C(6,8)], 126.9 [C(2') or C(3')], 127.2 [C(4')], 128.7 [C(3') or C(2')], 151.9 [C(1')]; $^{15}$N NMR (C$_6$D$_6$) ppm 55.68 [N(7)]; $^{77}$Se NMR (C$_6$D$_6$ @ 50° C.) ppm 2.38 [Se(3)]. Analysis calculated for C$_{19}$H$_{21}$NSe: C, 66.66; H, 6.18; N, 4.09; Se, 23.06. Found: C, 66.82; H, 6.34; N, 3.97; Se, 22.82.

(55)

EXAMPLE XVI 6,8-Di(2-thiophene)-3-selena-7-azabicyclo[3.3.1]nonane (56)

6,8-Di(2-thiophene)-3-selena-7-azabicyclo[3.3.1]-nonan-9-one (1.00 g, 2.71 mmol) and anhydrous hydrazine (95%, 1.0 g, 30 mmol) were dissolved in triethylene glycol (40 mL) which was contained in a jacketed flask equipped for distillation. By boiling water in the jacket, the reaction mixture was heated to 100° C. and stirred at this temperature for 2 hours. Potassium hydroxide (85%, 2.0 g, 30 mmol) was added in one portion and the water in the jacket then replaced by xylene which, when boiled, brought the temperature of the reaction mixture to 140°-145° C. Stirring was continued at this temperature for 5 hours. After cooling to room temperature, the reaction mixture was poured into ice-cold water (200 mL) after which a precipitate immediately formed. This mixture was set aside at room temperature overnight and was then filtered. The filtrate was taken up in boiling benzene and treated with decoloring carbon. The benzene was evaporated (aspirator) and the residue was recrystallized in 95% ethanol to give 0.64 g (67%) of 6,8-di(2-thiophene)-3-selena-7-azabicyclo[3.3.1]nonane as a light tan solid: mp 183°-185° C. (dec); IR (KBr) cm$^{-1}$ 3270 (N—H); $^1$H NMR (DCCl$_3$) δ1.28 [d, 1 H, H(9), J=13 Hz, 2 Hz], 1.78 [br s, 1 H, H(7)], 2.18 [br s, 2 H, H(1,5)], 2.32 [d, 2 H, H(2,4)$_{ax}$, J=12 Hz], 2.50 [m, 1 H, H(9)], 3.20 [dd, 2 H, H(2,4)$_{eq}$, J=13 Hz], 4.79 [d, 2 H, H(6,8), J=4 Hz], 6.96 [dd, 2 H, ArH], 7.01 [2 H, d, ArH], 7.21 [d, 2 H, ArH]; $^{13}$C NMR (DCCl$_3$) ppm 25.0 [C(2,4)], 25.8 [C(9)], 34.6 [C(1,5)], 57.1 [C(6,8)], 122.2 [C(4')], 122.6 [C(2')], 126.1 [C(3')], 150.7 [C(1')]; $^{15}$N NMR (DCCl$_3$) ppm 60.10 [N(7)]; $^{77}$Se NMR (DCCl$_3$) ppm 4.05 [Se(3)]. 6,8-Di(2-thiophene)-3-selena-7-azabicyclo[3.3.1]nonane proved difficult to purify for satisfactory analysis and was converted to 6,8-Diphenyl-3-selena-7-azabicyclo[3.3.1]-nonane Hydroperchlorate of Example XIX.

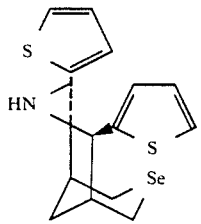

(56)

EXAMPLE XVII 6,8-Di(4-chorophenyl)-3-selena-7-azabicyclo[3.3.1]nonane (57)

Endo,exo 6,8-di(4-chlorophenyl)-3-selena-7-azabicyclo[3.3.1]nonan-9-one (the endo,exo isomer) (2.00 g, 4.71 mmol), anhydrous hydrazine (95%, 2.0 g, 60 mmol), and triethylene glycol (35 mL) were placed in a jacketed, round-bottomed flask along with a magnetic stirring bar. The contents of the flask were heated to 100° C. under a stream of nitrogen by boiling water in the jacket of the reaction flask. Stirring at this temperature was continued for 3 hours after which time potassium hydroxide (85%, 5.0 g, 76 mmol) was added in one portion. The reaction mixture was then heated to 140°-145° C. by boiling xylene in the jacket. After 4 hours at this temperature, the resulting solution was cooled (60°-70° C.) and was poured into water (100 mL) which precipitated a cream-colored solid. This solid was filtered and washed with water. Recrystallization (twice, absolute ethanol, deoclorizing carbon) gave 6,8-di(4-chlorophenyl)-3-selena-7-azabicyclo[3.3.1]nonane as a light tan solid (0.91 g, 47%): mp 179°-180° C. (dec); IR (KBr) cm$^{-1}$ 3260 (N—H); $^1$H NMR (DCCl$_3$) δ1.30 [d, 1 H, H(7), J=12 Hz], 1.74 [br s, 1 H, H(7)], 2.04 [br s, 2 H, H(1,5)], 2.28 [br d, 2 H, H(2,4)$_{ax}$, J=12 Hz], 2.48 [m, 1 H, H(9)], 3.17 [dd, 2 H, H(2,4)$_{eq}$, J=12 Hz, 4 Hz], 4.43 [d, 2 H, H(6,8), J=5 Hz], 7.26-7.50 [m, 8 H, ArH]; $^{13}$C NMR (DCCl$_3$) ppm 25.1 [C(2,4)], 26.9 [C(9)], 33.8 [C(1,5)], 60.9 [C(6,8)], 127.9, 128.6, 132.6 [C(4')], 145.7 [C(1')]; $^{15}$N NMR (DCCl$_3$) ppm 55.37 [N(7)]; $^{77}$Se NMR (DCCl$_3$) ppm −0.79 [Se(3)].

6,8-Di(4-chorophenyl)-3-selena-7-azabicyclo[3.3.1-]nonane proved exceedingly difficult to obtain in pure form and give a satisfactory analysis. Thus, it was converted to the hydroperchlorate salt 6,8-di(4-chlorophenyl)-3-selena-7-azabicyclo[3.3.1]nonane hydroperchlorate of Example XXI which analyzed well.

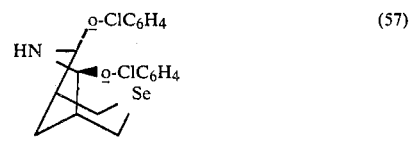

(57)

EXAMPLE XVIII 6,8-Di(4-chorophenyl)-3-selena-7-azabicyclo[3.3.1]nonane (58)

Endo,endo 6,8-di(4-chlorophenyl)-3-selena-7-azabicyclo[3.3.1]nonan-9-one (the endo,exo isomer) (2.00 g, 4.71 mmol), anhydrous hydrazine (95%, 2.0 g, 60 mmol), and triethylene glycol (35 mL) were placed in a 60-mL, two-necked, jacketed, round-bottomed flask along with a magnetic stirring bar. This mixture was heated to 100° C. by boiling water in the jacket of the reaction flask. Stirring at this temperature under a stream of nitrogen was continued for 2 hours at which time potassium hydroxide (85%, 5.0 g, 76 mmol) was added. The temperature of the resulting mixture was increased to 140°-145° C. by boiling xylene in the jacket of the reaction flask. After stirring at this temperature for 3 h, the resulting solution was cooled (60°-70° C. and was poured into water (100 mL). This precipitated a light yellow solid which was filtered and washed with water. This solid was recrystallized (absolute ethanol, decolorizing carbon) to give 6,8-di(4-chorophenyl)-3-selena-7-azabicyclo[3.3.1]nonane as a white powder (1.14 g, 59%): mp 163°-165° C. (dec); IR (KBr) cm$^{-1}$ 3290 (N—H); $^1$H NMR (CDCl$_3$) δ2.04 [br s, 2 H, H(1,5)], 2.18 [d, 1 H, H(9), J=14 Hz], 2.25 [d, 2 H, H(2,4)$_{ax}$, J=12 Hz], 2.36 [d, 1 H, H(9), J=13 Hz], 2.59 [br s, 1 H, H(7)], 3.04 [dd, 2 H, H(2,4)$_{eq}$, J=12 Hz, 4 Hz], 4.50 [d, 2 H, H(6,8), J=3 Hz], 7.32-7.52 [m, 8 H, ArH]; $^{13}$C NMR (CDCL$_3$) pmm 17.7 [C(2,4)], 30.4 [C(1,5)], 35.0 [C(9)], 64.0 [C(6,8)], 127.9, 128.5, 132.6 [C(4')], 141.1 [C(1')]; $^{15}$N NMR (CDCL$_3$) ppm 50.52 [N(7)]; $^{77}$Se NMR (CDCl$_3$) ppm 101.86 [Se(3)].

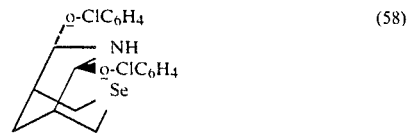

(58)

EXAMPLE XIX

6,8-Diphenyl-3-selena-7-azabicyclo[3.3.1]nonane Hydroperchlorate (59)

A solution was made of 6,8-diphenyl-3-selena-7-azabicyclo[3.3.1]nonane (0.63 g, 1.8 mmol) in benzene (100 mL). Perchloric acid (60%, 1.0 g, 6.0 mmol) was added dropwise, very slowly with swirling. The resulting mixture was allowed to stand at room temperature with occasional swirling for 3 hours. The orange solid which formed was filtered and recrystallized (methanol) to give 0.62 g (78%) of 6,8-diphenyl-3-selena-7-azabicyclo[3.3.1]nonane hydroperchlorate as white needles: mp 288.0°–289.0° C. (dec, sealed tube); $^1$H NMR (DMSO-$d_6$) δ1.78 [br d, 1 H, H(9), J=13.0 Hz], 2.36 [br d, 2 H, H(2,4)$_{ax}$, J=13.0 Hz], 2.59 [m, 3 H, H(1,5) and H(9)], 3.16 [dd, 2 H, H(2,4)$_{eq}$, J=12.0, 2.0 Hz], 4.73 [br d, 2 H, H(6,8), J=3.0 Hz], 7.19–7.70 [m, 10 H, ArH], 8.72 [m, 1 H, H(7)$_{ax}$], 9.67 [m, 1 H, H(7)$_{eq}$]; $^{13}$C NMR (DMSO-$d_6$) ppm 23.5 [C(2,4)], 26.6 [C(9)], 31.2 [C(1,5)], 61.5 [C(6,8)], 128.5, 128.7, 128.6, 137.0 [C(1')]; $^{15}$N NMR (DMSO-$d_6$) ppm 57.91 [N(7)]; $^{77}$Se NMR (DMSO-$d_6$) ppm 1.16 [Se(3)]. Analysis calculated for $C_{19}H_{22}ClNO_4Se$: C, 51.54; H, 5.01; N, 3.16; Se, 17.83. Found: C, 51.52; H, 4.94; N, 3.34; Se, 17.65.

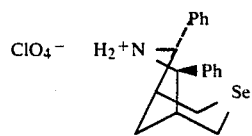

(59)

EXAMPLE XX

6,8-Di(2-thiophenyl)-3-selena-7-azabicyclo[3.3.1]nonane Hydroperchlorate (60)

A solution was made of 6,8-di(2-thiophene)-3-selena-7-azabicyclo[3.3.1]nonane (0.5 g, 1.4 mmol) in benzene (200 mL) and isopropyl alcohol (10 mL). To this solution was added 60% HClO$_4$ (0.5 g, 3.0 mmol) dropwise slowly causing a white precipitate to form. This precipitate quickly became yellow. The solvent was decanted and the solid was recrystallized twice (isopropyl alcohol, decolorized carbon) to give 0.4 g (63%) of 6,8-di(2-thiophenyl)-3-selena-7-azabicyclo[3.3.1]nonane hydroperchlorate as white needles: mp 285° C. (dec); $^1$H NMR (DMSO-$d_6$) δ1.78 [d, 1 H, H(9), J=14 Hz], 2.36 [d, 2 H, H(2,4)$_{ax}$, J=14 Hz], 2.44 [m, 1 H, H(9)], 2.66 [br s, 2 H, H(1,5)], 3.19 [dd, 2 H, H(2,4)$_{eq}$, J=12 Hz, 3 Hz], 5.07 [m, 2 H, H(6,8), 7.16 [dd, 2 H, H(3'), J=4 Hz, J=6 Hz], 7.43 [d, 2 H, H(2'), J=4 Hz], 7.69 [dd, 2 H, H(4'), J=3 Hz, J=6 Hz], 9.36 [br s, 1 H, H(7)], 9.61 [br s, 1 H, H(7)]; $^{13}$C NMR (DMSO-$d_6$) ppm 23.5 [C(2,4)], 26.2 [C(9)], 32.5 [C(1,5))], 56.1 [C(6,8)], 127.3 [C(2') of C(4')], 127.6 [C(4')] or C(2')], 129.2 [C(3')], 138.9 [C(1')]; $^{15}$N NMR (DMSO-$d_6$) ppm 62.39 [N(7)]; $^{77}$Se NMR (DMSO-$d_6$) ppm 5.11 [Se(3)]. Analysis calculated for $C_{15}H_{18}ClNO_4S_2Se$: C, 39.61; H, 3.99; N, 3.08; S, 14.10; Se, 17.36. Found: C, 39.81; H, 3.97; N, 3.10; S, 14.35; Se, 17.18.

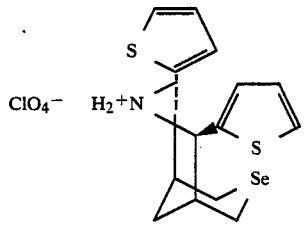

(60)

EXAMPLE XXI

6,8-Di(4-chlorophenyl)-3-selena-7-azabicyclo[3.3.1]nonane Hydroperchlorate (61)

6,8-Di(4-chorophenyl)-3-selena-7-azabicyclo[3.3.1]nonane (1.00 g, 2.43 mmol) was dissolved in ether (200 mL). Perchloric acid (60%, 1.0 g, 6.0 mmol) was added slowly with vigorous swirling. The resulting mixture was allowed to stand for 24 hours with occasional swirling. The yellow-orange solid which formed was filtered and recrystallized (twice, absolute ethanol, decolorizing carbon) to give 6,8-di(4-chlorophenyl)-3-selena-7-azabicyclo[3.3.1]nonane hydroperchlorate as a white powder (0.46 g, 37%): mp 272°–274° C. (dec); $^1$H NMR (DMSO-$d_6$) δ1.77 [d, 1 H, H(9), J=12.0 Hz], 2.36 [d, 2 H, H(2,4)$_{ax}$, J=10.8 Hz], 2.53 [m, 2 H, H(1,5)], 3.14 [d, 2 H, H(2,4)$_{eq}$, J=10.5 Hz], 3.38 [br s, 1 H, H(9)], 4.76 [br s, 2 H, H(6,8)], 7.50–7.75 [m, 8 H, ArH], 8.77 [br s, 1 H, H(7)], 9.59 [br s, 1 H, H(7)]; $^{13}$C NMR (DMSO-$d_6$) ppm 23.5 [C(2,4)], 26.5 [C(9)], 31.1 [C(1,5)], 60.6 [C(6,8)], 128.5, 130.9, 133.8 [C(4')], 136.1 [C(1')]; $^{15}$N NMR (DMSO-$d_6$) ppm 57.67 [N(7)]; $^{77}$Se NMR (DMSO-$d_6$) ppm 2.25 [Se(3)]. Analysis calculated for $C_{19}H_{20}Cl_3NO_4Se$: C, 44.60; H, 3.94; N, 2.47. Found: C, 44.53; H, 3.84; N, 2.74.

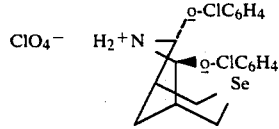

(61)

EXAMPLE XXII

6,8-Di(2-chlorophenyl)-3-selena-7-azabicyclo[3.3.1]nonane Hydroperchlorate (62)

6,8-Di(4-chorophenyl)-3-selena-7-azabicyclo[3.3.1]nonane (1.00 g, 2.43 mmol) was dissolved in ether (200 mL) in a 500 mL, round-bottomed flask. Perchloric acid (60%, 1.0 g, 6.0 mmol) was added slowly with swirling. The resulting mixture was allowed to stand at room temperature for 24 hours with occasional swirling. The orange solid which formed was filtered and recrystallized (absolute ethanol, decolorizing carbon) to give 6,8-di(2-chlorophenyl)-3-selena-7-azabicyclo[3.3.1]nonane hydroperchlorate (0.36 g, 29%) as white needles: mp 264°–265° C. (dec); $^1$H NMR (DMSO-$d_6$) δ2.16 [d, 1 H, H(9), J=12.1 Hz], 2.29 [d, 2 H, H(2,4)$_{ax}$, J=12.7 Hz], 2.50 [m, 3 H, H(1,5), H(9)], 3.13 [d, 2 H, H(2,4)$_{eq}$, J=12.3 Hz], 5.07 [d, 2 H, H(6,8), J=8.5 Hz], 7.58–7.90 [m, 8 H, ArH], 9.18 [br s, 1 H, H(7)], 10.46 [br s, 1 H, H(7)]; $^{13}$C NMR (DMSO-$d_6$) ppm 17.7 [C(2,4)], 29.7 [C(1,5)], 32.0 [C(9)], 63.7 [C(6,8)], 128.6, 128.9, 133.2 [C(4')], 134.5 [C(1')]; $^{15}$N NMR (DMSO-$d_6$) ppm 49.57 [N(7)]; $^{77}$Se NMR (DMSO-$d_6$) ppm 74.96 [Se(3)]. Anal-

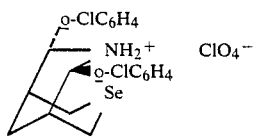

(62)

EXAMPLE XXIII

N,N'-Dibenzyl-3,7-diazabicyclo[3.3.1]nonan-9-one (63)

Following a procedure similar to that disclosed in U.S. Pat. No. 3,962,449, a three-necked, 50-mL, round-bottomed flask was fitted with a dropping funnel (60 mL), a condenser with an $N_2$ inlet, a heating mantle, and a magnetic stirrer. This flask was charged with a solution of benzylamine (2.68 g, 25.0 mmol) and glacial acetic acid (1.54 g, 25.8 mmol) in methanol (25 mL). To this solution was added paraformaldehyde (1.58 g, 52.5 mmol); then the apparatus was flushed with $N_2$ and the mixture was brought to reflux with stirring. After 15 min, a solution of 1-benzyl-4-piperidone (4.73 g, 25.0 mmol) and glacial acetic acid (1.50 g, 25.0 mmol) in methanol (18 mL) was added over 0.5 hours. The resulting orange solution was then boiled at reflux for an additional 9.5 hours. The mixture was then cooled to room temperature and the solvent was evaporated (aspirator) to give an orange oil. Water (50 mL) and KOH pellets (85%, 3.30 g, 50.0 mmol) were added, and the resulting oily, orange suspension was extracted ($CH_2Cl_2$, 3×50 mL). The organic extracts were combined and dried ($MgSO_4$, overnight). Filtration of the mixture followed by evaporation (aspirator) afforded an orange oil which was vacuum distilled ($8 \times 10^{-7}$ mm Hg, diffusion pump). At 106°–108° C. there was collected a colorless oil (0.36 g), the $^{13}C$ NMR of which was identical to 1-benzyl-4-piperidone. A second fraction (bp 180°–205° C.) was collected as a yellow oil but with substantial decomposition of the residue. This second fraction was redistilled (180°–185° C., $1.0 \times 10^{-6}$ mm Hg) to yield again a yellow oil. This oil was dissolved in hot Skelly B (80 mL) and, upon cooling to −10° C., pure N,N'-dibenzyl-3,7-diazabicyclo[3.3.1]nonan-9-one (2.53 g, 31.6%) was precipitated as a white solid: mp 61°–63° C. (literature 70°–71° C.). The compound was used in the next step without further purification. The spectroscopic data for this compound were: IR (KBr) $cm^{-1}$ 2963, 2822, 1738, 1721, 748, 703 $^1H$ NMR ($DCCl_3$) δ2.52 [br s, 2 H, H(1,5)], 2.77, 2.78 [two d, J=10.7 Hz, 4 H, H(2,4,6,8)ax], 3.00 [br d, J=10.5 Hz, 4 H, H(2,4,6,8)eq], 3.53 [s, 4 H, ArC$\underline{H}_2$], 7.23–7.30 [m, 10 H, ArH]; $^{13}C$ NMR ($DCCl_3$) ppm 46.7 [d, C(1,5)], 58.01 [t, C(2,4,6,8)], 61.1 [t, ArC$\underline{H}_2$], 126.90 [d, p-Ar$\underline{C}$], 128.02 [d, o- or m-Ar$\underline{C}$], 128.53 [d, m- or o-Ar$\underline{C}$] 138.02 [s, i-Ar$\underline{C}$], 214.0 [s, C(9)]; $^{15}N$ NMR ($DCCl_3$) ppm 39.25 [N(3,7)].

EXAMPLE XXIV

N,N'-Dibenzyl-3,7-diazabicyclo[3.3.1]nonan-9-one (63)

In a minor modification of the previous procedure, a solution of 1-benzyl-4-piperidone (4.73 g, 25.0 mmol) and glacial acetic acid (1.50 g, 25.0 mmol) in methanol (25 mL) was added as before to a boiling mixture of paraformaldehyde (6.00 g, 200 mmol), glacial acetic acid (1.62 g, 27.0 mmol), benzylamine (2.68 g, 25.0 mmol), and methanol (100 mL). The reaction time was 24 hours and the aqueous workup was as described previously. Instead of the distillation described, the crude oil from the workup was then digested in Skelly B (300 mL) on a steam bath for 0.5 hours. The hot supernatant was decanted from the yellow residue and evaporated (aspirator followed by vacuum pump, room temperature 0.02 mm Hg, 20 min). This afforded N,N'-dibenzyl-3,7-diazabicyclo[3.3.1]nonan-9-one (6.84 g, 85.4%) as a white oil that did not solidify after 3 days at −10° C. The $^1H$ and $^{13}C$ NMR spectra of this oil were virtually identical to that described for the ketone produced in Example XXIII via method A and the material proved to be satisfactory for use in the following Examples XXV and XXVI.

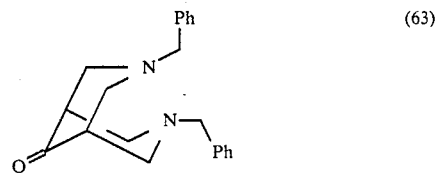

(63)

EXAMPLE XXV

N,N'-Dibenzyl-3,7-diazabicyclo[3.3.1]nonane Hydroperchlorate (64)

Following a procedure similar to that disclosed in U.S. Pat. No. 3,962,449 for the synthesis of N,N'-dibenzyl-3,7-diazabicyclo[3.3.1]nonane, a jacketed, two-necked, 70-mL flask was fitted with a lower take-off condenser with an $N_2$ inlet and a receiving flask, a thermometer, a condenser on the jacket, a magnetic stirrer, and a heating mantle. This flask was charged with N,N'-dibenzyl-3,7-diazabicyclo[3.3.1]nonan-9-one (2.00 g, 6.24 mmol), hydrazine hydrate (85%, 1.10 g, 18.7 mmol), KOH pellets (85%, 2.06 g, 31.2 mmol), and triethylene glycol (25 mL). The apparatus was flushed with $N_2$, and the mixture heated at 120° C. for 0.5 hours using tetralin (bp 207° C.) in the jacket. The reaction mixture was then allowed to boil at reflux for 5 hours. The temperature slowly increased to 207° C. with removal of the volatile distillates and with the evolution of $N_2$. The reaction mixture was cooled to room temperature and was poured, along with the distillate, into cool water (30 mL), which resulted in the formation of a white suspension. This was extracted (ether, 4×30 mL), and the combined extracts were washed successively with NaOH solution (10%, 30 mL), $H_2O$ (30 mL), and NaCl solution (saturated, 30 mL). After drying ($Na_2SO_4$, overnight), the solution was filtered and evaporated (aspirator) to give the crude amine, N,N'-dibenzyl-3,7-diazabicyclo[3.3.1]nonane as a yellow oil (1.34 g, 70.1%). This oil was dissolved in $C_6H_6$ (20 mL) and treated dropwise over 15 min with a solution of $HClO_4$ (60%, 2.20 g, 13.1 mmol) in 2-propanol (5 mL) to give a dark solution. This solution was stirred (magnetic) for 1 hour after which it was concentrated (5 mL). Addition of ether (20 mL) precipitated the salt as a dark brown solid. Filtration and recrystallization (aqueous ethanol, 20 mL, decolorizing carbon) afforded a first crop of N,N'-dibenzyl-3,7-diazabicyclo[3.3.1]nonane hydroperchlorate (0.652 g) as the monoperchlorate; mp 221°–222° C. Concentration of the mother liquor to 7 mL gave a second crop (0.126 g, total: 0.778 g, 43.7% total), mp 220°–222° C. The spectroscopic data for this compound were: IR (KBr) cm$^{-1}$ 2960, 2841 (C—H), 2800–2600 (N$^+$—H), 1100, 1080 (Cl—O); $^1$H NMR (DMSO-d$_6$) δ1.72 [br s, 2 H, H(9)], 2.14 [br s, 2 H, H(1,5)], 2.77 [d, J=13 Hz, 4 H, H(2,4,6,8)]ax], 3.13 [d, J=13 Hz, 4 H, H(2,4,6,8)eq], 3.43 [br s, 1 H, N$^+$—H], 3.86 [s, 4 H, ArC$\underline{H}$$_2$], 7.30–7.48 [m, 10 H, Ar$\underline{H}$]; $^{13}$C NMR (DMSO-d$_6$) ppm 27.4 [d, C(1,5)], 29.54 [t, $\underline{C}$(9)], 56.97 [t, C(2,4,6,8)], 60.4 [t, Ar$\underline{C}$H$_2$], 128.2 [d, p-Ar$\underline{C}$], 128.4 [d, o- or m-Ar$\underline{C}$], 129.6 [d, m- or o-Ar$\underline{C}$], 133.30 [s, i-Ar$\underline{C}$]; $^{15}$NMR (DMSO-d$_6$) ppm 54.59 [N(3,7)]. Analysis calculated for C$_{21}$H$_{27}$ClN$_2$O$_4$: C, 61.99; H, 6.69; Cl, 8.71; N, 6.88. Found: C, 61.92; H, 6.84; Cl, 8.71, N, 6.82. [Although the N,N'-dibenzyl-3,7-diazabicyclo[3.3.1]nonane hydroperchlorate was supposedly synthesized (see Ruenitz, P. C. and Smissman, E. E. *J. Heterocy. Chem.* 1976, 13, 1111), the material was not a true pure compound since it had a melting range of 210°–217° C. and orange crystals were reported; therefore, the above data is for the true, pure compound]

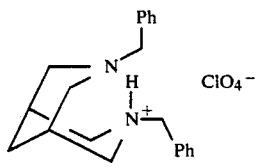

(64)

EXAMPLE XXVI

N,N'-Dibenzyl-9,9-dimethoxy-3,7-diazabicyclo[3.3.1]nonane Hydroperchlorate (65)

A one-necked, 100-mL, round-bottomed flask was equipped with a Soxhlet containing 3A molecular sieve (30 g), a condenser with N$_2$ inlet, a magnetic stirrer and a heating mantle. The effective cycling volume of the Soxhlet was approximately 20 mL. The flask was charged with a solution of N,N'-dibenzyl-3,7-diazabicyclo[3.3.1]nonan-9-one (1.00 g, 3.12 mmol) in CH$_3$OH (25 mL) and C$_6$H$_6$ (25 mL) to which was added HClO$_4$ (60%, 1.50 g, 8.96 mmol) in one portion. The volume of the methanol used was such that the perchloric acid always remained in solution and did not become completely dry. The apparatus was flushed with N$_2$ and the colorless solution was heated to reflux with cycling through the Soxhlet. After 24 h, the now pale yellow solution was cooled to room temperature and concentrated to about 5 mL. Upon standing for a few minutes, a product precipitated as a white solid which was filtered, washed with C$_6$H$_6$ (10 mL), and recrystallized (CH$_3$OH, 80 mL) to afford the monoperchlorate N,N'-dibenzyl-9,9-dimethoxy-3,7-diazabicyclo[3.3.1]nonane hydroperchlorate (0.9103 g) as small white crystals, mp 223.6°–224.0° C. (dec). The mother liquor was concentrated to approximately 10 mL. Upon cooling at −10° C. overnight, a second crop of N,N'-dibenzyl-9,9-dimethoxy-3,7-diazabicyclo[3.3.1]nonane hydroperchlorate was obtained (89.4 mg, total: 0.9997 g, 68.6% total), mp 219°–220° C. (dec). The spectral data were as follows: IR (KBr) cm$^{-1}$ 2800–2600 (N$^+$—H), 1100 (Cl—O); $^1$H NMR (DMSO-d$_6$) δ2.35 [br s, 2 H, H(1,5)], 2.90 [d, J=13 Hz, 4 H, H(2,4,6,8)ax], 3.08 [d, J=13, 4 H, H(2,4,6,8)eq], 3.14 [s, 6 H, CH$_3$O], 3.88 [s, 4 H, ArC$\underline{H}$$_2$], 7.38–7.54 [m, 10 H, Ar$\underline{H}$], 9.84 [br s, 1 H, N$^+$—$\underline{H}$]; $^{13}$C-NMR (DMSO-d$_6$) ppm 33.0 [d, C(1,5)], 46.96 [q, $\underline{C}$H$_3$O], 53.8 [t, C(2,4,6,8)], 59.56 [t, Ar$\underline{C}$H$_2$], 95.36 [s, $\underline{C}$(9)], 128.22 [d, p-Ar$\underline{C}$], 128.4 [d, o- or m-Ar$\underline{C}$], 129.62 [d, m- or o-Ar$\underline{C}$], 133.45 [s, i-Ar$\underline{C}$]; $^{15}$N NMR DMSO-d$_6$) ppm 52.89 [N(3,7)]. Analysis calculated for C$_{23}$H$_{31}$ClN$_2$O$_6$: C, 59.16; H, 6.69; Cl, 7.59; N, 6.00. Found: C, 58.98; H, 6.81; Cl, 7.86; N, 6.28.

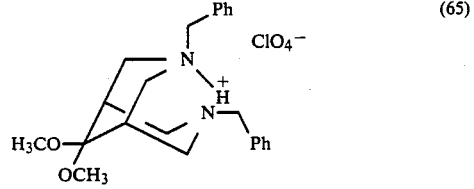

(65)

EXAMPLE XXVII

7-Benzyl-9,9-dimethoxy-3-thia-7-azabicyclo[3.3.1]nonane Hydroperchlorate (66)

A one-necked, 100-mL round-bottomed flask was fitted with a Soxhlet containing 3A molecular sieves (30 g), a condenser, an N$_2$ inlet, a heating mantle, a magnetic stirrer, and a heating mantle. The effective cycling volume of the Soxhlet was approximately 15 mL. The flask was charged with a solution of N-benzyl-3-thia-7-azabicyclo[3.3.1]nonan-9-one [1.00 g, 4.04 mmol] in methanol (20 mL) and benzene (20 mL). To this solution was added HClO$_4$ (60%, 2.03 g, 12.1 mmol) in one portion. The volume of the methanol used was such that the perchloric acid always remained in solution and did not become completely dry. The apparatus was flushed with N$_2$ and the pale yellow solution was heated at reflux with stirring and cycling through the Soxhlet for 24 hours. The solution was cooled to room temperature and concentrated to about 5 mL. Ether (20 mL) was added, thus precipitating the salt as a powder. This was filtered, washed with ether (5 mL), and dissolved in hot methanol (20 mL, decolorizing carbon). Trituration with ether (25 mL), followed by standing for 24 h, afforded 7-benzyl-9,9-dimethoxy-3-thia-7-azabicyclo[3.3.1]nonane hydroperchlorate (0.7345 g, 46.2%) as small white crystals: mp 193°–194° C. (dec); IR (KBr) cm$^{-1}$ 2800–2600 (N$^+$—H), 1090 (Cl—O); $^1$H NMR (DMSO-d$_6$) δ2.58 [br s, 2 H, H(1,5)], 2.75 [d, J=14 Hz, 2 H, H(2,4)ax], 3.15–3.18 [m, 8 H, H(2,4)eq,CH$_3$O], 3.38 [dd or br t, J=12 Hz, 2 H, H(6,8)ax], 3.60 [d, J=12 Hz, H(6,8)eq], 4.33 [d, J=5 Hz, 2 H, ArC$\underline{H}$$_2$], 7.49–7.62 [m, 5 H, Ar$\underline{H}$], 9.28 [br s, 1 H, N$^+$—$\underline{H}$]; $^{13}$C NMR (DMSO-d$_6$) ppm 28.78 [t, C(2,4)], 32.20 [d, C(1,5)], 46.60 [q, $\underline{C}$H$_3$O], 47.00 [q, $\underline{C}$H$_3$O], 54.42 [t, C(6,8)], 60.24 [t, Ar$\underline{C}$H$_2$], 95.1 [s, C(9)], 129.0 [d, o- or m-Ar$\underline{C}$], 129.46 [s, i-Ar$\underline{C}$], 130.1 [d, p-Ar$\underline{C}$], 130.2 [d, m- or o-Ar$\underline{C}$]; $^{15}$N NMR (DMSO-d$_6$) ppm 53.49 [N(7)]. Analysis calculated for C$_{26}$H$_{24}$ClNO$_6$: C, 48.79; H, 6.14; Cl, 9.00; N, 3.56; S, 8.14. Found: C, 48.73; H, 6.09; Cl, 9.39; N, 3.54; S, 8.40.

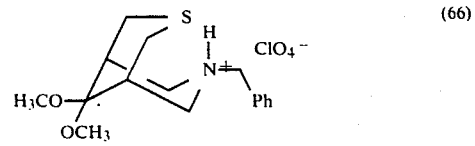

(66)

EXAMPLE XXVIII endo,exo- and endo,endo-7-Benzyl-2,4-bis(2-chlorophenyl)-3,7-diazabicyclo[3.3.1]nonan-9-ones (67),(68)

A three-necked, 50 mL, round-bottomed flask was fitted with a condenser, an addition funnel, a thermometer, magnetic stirrer, a heating mantle, and an $N_2$ inlet. This flask was charged with ammonium acetate ($NH_4OAc$, 2.31 g, 30.0 mmol) and ethanol (10 mL) and the flask flushed with $N_2$. The slurry was warmed to 40° C. with stirring until all $NH_4OAc$ dissolved, then the solution was cooled to room temperature. A solution of 2-chlorobenzaldehyde (5.67 g, 40.3 mmol), 1-benzyl-4-piperidone (3.78 g, 20.0 mmol), and deoxygenated ethanol (15 mL) was added in one portion. The resulting solution was slowly warmed to 70° C. over 30 minutes. Upon cooling to room temperature, a white precipitate (solid A) formed which was filtered and washed with dry ether (20 mL). These washings were combined with the original filtrate and this solution was cooled at −10° C. for 1 hour to give a second solid precipitate (solid B) which was also filtered and set aside. Evaporation of the filtrate afforded an oily orange solid which was dissolved in ether (10 mL). Upon standing for 1 hour at −10° C., a third white solid (solid C) precipitated. This too was filtered and set aside. Upon standing for 24 h, a fourth white solid (solid D) was precipitated, which was also filtered and set aside. Upon standing for 22 days at −10° C., a small amount of a fifth solid (solid E) precipitated which was treated as before.

Solid A was recrystallized (2-propanol/$HCCl_3$, 3:1, 40 mL) to afford pure endo,exo-3-7-benzyl-2,4-bis(2-chlorophenyl)-3,7-diazabicyclo[3.3.1]nonan-9-one (1.06 g) as long white needles: mp 184°–185° C.; IR(KBr) cm$^{-1}$ 3340 (N—H), 1733 (C=O); $^1$H NMR ($DCCl_3$) d 1.61 [s, 1 H, N—H], 2.54, 2.56 [overlapping d, J=12 Hz, and br s, 4 H, H($\overline{1,5}$) and H(6,8)ax], 3.49 [d, J=12 Hz, 2 H, H(6,8)eq], 3.73 [s, 2 H, ArCH$_2$], 5.50 [br s, 2 H, H(2,4)], 7.14–7.80 [m, 13 H, Ar$\overline{H}$]; $^{13}$C NMR ($DCCl_3$) ppm 55.15 [d, C(1,5)], 58.77 [t, $\overline{C(6,8)}$], 59.02 [d, C(2,4)], 60.99 [t, ArCH$_2$], 127.35, 127.48, 128.38, 128.44, 128.59, 129.16, 129.$\overline{21}$, 132.15, 138.35, 142.63 [ArC], 211.95 [s, C(9)]; $^{15}$N NMR ($DCCl_3$) ppm 38.31 [$\overline{N}$(7)], 58.24 [N(3)].

Solids B, C and E were combined and recrystallized (2-propanol/$HCCl_3$, 3:1, 15 mL) to afford additional endo,exo-3-7-benzyl-2,4-bis(2-chlorophenyl)-3,7-diazabicyclo[3.3.1]nonan-9-one (0.50 g, total: 1.56 g, 17.3%) mp 184°–185° C. Solid D was also recrystallized from the same solvent system (15 mL) to afford endo,endo-7-benzyl-2,4-bis(2-chlorophenyl)-3,7-diazabicyclo[3.3.1]nonan-9-one (0.36 g, 4.0%) as short white needles: mp 209.5°–210.0° C.; IR (KBr) cm$^{-1}$ 3270 (N—H), 1717 (C=O); $^1$H NMR ($DCCl_3$) δ2.54 [d, J=12 Hz, 2 H, H(6,8)ax], 2.76 [br s, 2 H, H(1,5)], 3.12 [d, J=12 Hz, 2 H, H(6,8)eq], 3.32 [s, 2 H, ArCH$_2$], 4.70 [br s, 1 H, N—H], 4.80 [br s, 2 H, H(2,4)], $\overline{7.15}$–7.60 [m,ArH]; $^{13}$C NMR ($DCCl_3$) ppm 50.90 [d, C(1,5)], 55.50 [$\overline{t}$, C(6,8)], 62.11 [d, C(2,4)], 62.54 [t, ArCH$_2$], 126.62, 127.44, 128.45, 128.57, 129.75, 129.81, 1$\overline{2}$9.90, 132.32, 136.66, 137.22 [Ar$\overline{C}$], 212.22 [s, C(9)]; $^{15}$N NMR ($DCCl_3$) ppm 46.90 [N(7)]$\overline{,}$ 54.45 [N(3)]. Analysis calculated for the endo, exo- isomer $C_{26}H_{24}Cl_2N_2O$: C, 69.18; H, 5.36; Cl, 15.71; N, 6.21. Found: C, 69.31, H, 5.20; Cl, 15.83; N, 6.18. Analysis calculated for the endo, endo-7-benzyl-2,4-bis(2-chlorophenyl)-3,7-diazabicyclo[3.3.1]nonan-9-one of 17 Calcd. for $C_{26}H_{24}Cl_2N_2O$: C, 69.18; H, 5.36; Cl, 15.71; N, 6.21. Found: C, 69.33; H, 5.53; Cl, 15.97; N, 6.09.

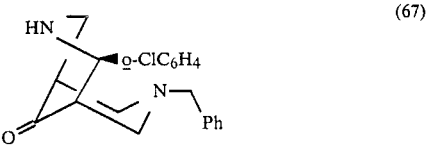

(67)

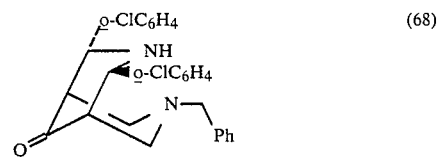

(68)

EXAMPLE XXIX endo,exo-7-Benzyl-2,4-bis(2-chlorophenyl)-3,7-diazabicyclo[3.3.1]nonan-9-one (67)

A one-necked, 50-mL, round-bottom flask was fitted with a condenser, a magnetic stirrer, and an $N_2$ inlet at the top of the condenser. The flask was charged with 95% ethanol (50 mL) and the apparatus was flushed with $N_2$. This solvent was heated at reflux for 0.5 hours. Upon cooling to room temperature, 1-benzyl-4-piperidone (4.73 g, 25.0 mmol), 2-chlorobenzaldehyde (7.03 g, 50.0 mmol), and ammonium acetate (5.78 g, 75.0 mmol) were added to the flask. The apparatus was again flushed with $N_2$ and the mixture was allowed to stir at room temperature. The $NH_4OAc$ slowly dissolved over 1 hour and the formation of a small amount of white precipitate was noted shortly thereafter. Continued stirring at room temperature for 5 days gave additional white precipitate while the supernatant slowly developed a bright red-orange color. The precipitate (solid A) was filtered and washed with ether (50 mL). The washings were combined with the original filtrate. This solution was cooled at −10° C. for 2 days, thus precipitating additional white solid (solid B) which was filtered and washed with ether. The filtrate was evaporated (aspirator) to give an orange gum. Ether (100 mL) was added and the mixture was heated on a steam bath until a third, almost white solid separated from the orange supernatant. This was filtered, washed with ether and recrystallized (2-propanol/$HCCl_3$, 3:1, 10 mL) to afford endo,endo-7-benzyl-2,4-bis(2-chlorophenyl)-3,7-diazabicyclo[3.3.1]nonane (0.1983 g, 1.8%) as tiny needles, mp 207°–209° C.

Solid A was recrystallized (2-propanol/$HCCl_3$, 3:1, 110 mL) to afford (3.14 g) as long white needles, mp 184.0°–184.5° C. Solid B was recrystallized in the same solvent system (15 mL) to give endo,exo-7-benzyl-2,4-bis(2-chlorophenyl)-3,7-diazabicyclo[3.3.1]nonan-9-one (0.40 g, total: 3.54 g, 31.3%), mp 184°–185° C. The IR, $^1$H and $^{13}$C NMR spectra for these products were identical to those given previously.

EXAMPLE XXX endo,exo-7-Benzyl-2,4-bis(2-chlorophenyl)-3,7-diazabicyclo[3.3.1]nonane (69)

A two-necked, jacketed flask with an $N_2$ inlet was fitted with a thermometer, a lower take-off condenser, a magnetic stirrer, a heating mantle, and a condenser on the jacket. The flask was charged with endo,exo-7-benzyl-2,4-bis(2-chlorophenyl)-3,7-diazabicyclo[3.3.1]nonan-9-one (0.80 g, 1.8 mmol) and triethylene glycol (50 mL), and the jacket charged with tetralin (bp 207°). The apparatus was flushed with N$_2$ and warmed to 110° C. with stirring to dissolve the ketone. To this solution was added in one portion hydrazine hydrate (85%, 0.52 g, 10.4 mmol), and the resulting solution was stirred at 110° C. for 1 hour. Potassium hydroxide pellets (85%, 5.00 g) were then added. The mixture was heated to 195° C. over 4.5 hours until N$_2$ evolution ceased, with the continuous distillation of volatiles. Upon cooling to room temperature, the tan solution was poured into H$_2$O (50 mL), and the resulting suspension was extracted with ethyl ether (5×30 mL). The combined ether extracts were washed with NaOH solution (10%, 50 mL) and dried (Na$_2$SO$_4$, overnight). Filtration followed by evaporation (aspirator) of the filtrate afforded a yellow oil which was dissolved in hot ethanol (25 mL). Upon cooling, the product precipitated as white plates which were filtered and dried to afford exo,exo-7-benzyl-2,9-bis(2-chlorophenyl)-3,7-azabicyclo[3.3.1-]nonane (0.54 g, 69%): mp 136.4°–137.0° C.; IR (KBr) cm$^{-1}$ 3300 (N—H); $^1$H NMR (DCCl$_3$) δ1.07 [dt, J=12.3, 2.7 Hz, 1 H, H(9)endo], 1.18 [br s, 1 H, N—H], 1.83 [br s, 2 H, H(1,5)], 2.09 [d, J=10 Hz, 2 H, H(6,8)ax], 2.35 [d, J=12.3 Hz, 1 H, H(9)exo], 3.08 [d, J=10 Hz, 2 H, H(6,8)ax], 3.50 [s, 2 H, ArCH$_2$], 4.77 [d, J=2.5 Hz, 2 H, H(2,4)], 7.09–7.92 [m, 13 H, ArH]; $^{13}$C NMR (DCCl$_3$) ppm 24.55 [b, C(9)], 36.13 [d, C(1,5)], 56.08 [d, C(2,4)], 58.76 [t, C(6,8)], 62.85 [t, ArCH$_2$], 126.79, 126.97, 127.52, 128.02, 128.08, 129.14, 129.27, 132.38, 139.19, 145.66 [ArC]; $^{15}$N NMR (DCCl$_3$) ppm 38.15 [N(7)], 50.48 [N(3)]. Analysis calculated for C$_{26}$H$_{26}$N$_2$Cl$_2$: C, 71.39; H, 6.00; N, 6.40; CL, 16.21. Found: C, 71.17; H, 6.25; N, 6.32; Cl, 16.15.

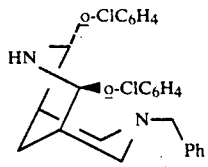

(69)

EXAMPLE XXXI endo,endo-7-Benzyl-2,4-bis(2-chlorophenyl)-3,7-diazabicyclo[3.3.1]nonane (70)

A jacketed two-necked flask with an N$_2$ inlet was fitted with a thermometer, a lower take-off condenser with receiving flask, a magnetic stirrer, a heating mantle, and a condenser on the jacket. This flask was charged with endo,endo-7-benzyl-2,4-bis(2-chlorophenyl)-3,7-diazabicyclo[3.3.1]nonane (1.87 g, 4.15 mmol) and triethylene glycol (75 mL) and the jacket charged with tetralin. The apparatus was flushed with N$_2$, and the mixture was heated to 110° C. with stirring to dissolve the ketone. Hydrazine hydrate (85%, 1.22 g, 20.7 mmol) was added in one portion and the resulting solution was heated at 110°–120° C. for 1 hour. Potassium hydroxide pellets (85%, 8.8 g) were then added and the resulting mixture was heated to 195° C. over 4 hours with the distillation of volatiles and the evolution of N$_2$. After cooling to room temperature, the solution was poured into H$_2$O (50 mL) and the resulting suspension was extracted with ether (7×50 mL). The combined ether extracts were washed with NaOH solution (10%, 100 mL) and dried (K$_2$CO$_3$, overnight). Filtration, followed by evaporation (aspirator), of the filtrate gave a yellow oil which was dissolved in warm ethanol (50 mL). Trituration with ether afforded, upon cooling, white cubic crystals which were filtered, washed with ether, and dried to give endo,endo-7-benzyl-2,4-bis(2-chlorophenyl)-3,7-diazabicyclo[3.3.1]nonane (1.11 g, 61%): mp 149°–151° C.; IR (KBr) cm$^{-1}$ 3250 (N—H); $^1$H NMR (DCCl$_3$) δ2.04 [br s, 2 H, H(1,5)], 2.06 [d, J=10 Hz, 1 H, H(9)], 2.17 [d, J=10 Hz, 2 H, H(6,8)ax], 2.29 [d, J=10 Hz, 1 H, H(9)], 2.82 [d, J=10 Hz, 2 H, H(6,8)eq], 3.10 [s, 2 H, ArCH$_2$], 4.44 [br s, 1 H, N—H], 4.68 [br s, 2 H, H(2,4)], 7.08–7.44 [m, 13 H, ArH]; $^{13}$C NMR (DCCl$_3$) ppm 31.50 [d, C(1,5)], 35.87 [t, C(9)], 54.86 [t, C(6,8)], 61.63 [d, C(2,4)], 64.31 [t, ArCH$_2$], 126.46, 127.33, 127.54, 128.25, 129.34, 129.80, 132.34, 138.04, 140.20 [ArC]; $^{15}$N NMR (DCCl$_3$) ppm 47.43 [N(7)], 53.80 [N(3)]. Analysis calculated for C$_{26}$H$_{26}$Cl$_2$N$_2$: C, 71.39; H, 6.00; Cl, 16.21; N, 6.40. Found: C, 71.48; H, 6.04; Cl, 16.00; H, 6.65.

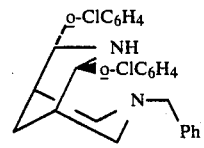

(70)

EXAMPLE XXXII endo,exo-7-Benzyl-2,4-bis(2-chlorophenyl)-3,7-diazabicyclo[3.3.1]nonane Hydroperchlorate (71)

In a one-necked, 100-mL, round-bottomed flask, a solution of endo,exo-7-benzyl-2,4-bis(2-chlorophenyl)-3,7-diazabicyclo[3.3.1]nonane (0.80 g, 1.83 mmol) in C$_6$H$_6$ (30 mL) was treated dropwise slowly with a solution of HClO$_4$ (60%, 1.50 g, 8.96 mmol) in 2-propanol (5 mL) which resulted in the formation of a white powdery precipitate. The flask was fitted with a condenser, and the mixture was heated on a steam bath for 15 min. After cooling to room temperature, the precipitate was filtered and recrystallized in a minimum amount of 70% acetone to afford the monohydroperchlorate endo,exo-7-benzyl-2,4-bis(2-chlorophenyl)-3,7-diazabicyclo[3.3.1]nonane hydroperchlorate as fine white crystals: mp 246°–247° C. (dec); IR (KBr) cm$^{-1}$ 3330 (N—H), 2900–2600 (N$^+$—H), 1110 (Cl—O); $^1$H NMR (DMSO-d$_6$) δ1.70 [d, J=14 Hz, 1 H, H(9)endo], 2.33 [d, J=11 Hz, 2 H, H(6,8)ax], 2.38 [br s, 2 H, H(1,5)], 2.51 [overlapping d, J=14 Hz, H(9)exo and br s, DMSO], 2.85 [d, J=11 Hz, 2 H, H(6,8)eq], 3.70 [s, 2 H, ArCH$_2$], 5.00 [d, J=8 Hz, H(2,4)], 7.32–7.94 [m, 13 H, ArH], 8.10 [br s, 1 H, N—H], 9.84 [br s, 1 H, N$^+$—H]; $^{13}$C NMR (DMSO-d$_6$) ppm 24.54 [t, C(9)], 33.70 [d, C(1,5)], 55.94 [t, C(6,8)], 56.85 [d, C(2,4)], 60.93 [t, C(10)], 127.55–130.88 [m, ArC], 132.63, 135.51, 137.09 [ArC]; $^{15}$NMR (DMSO-d$_6$) ppm 38.30 [N(7)], 54.60 [N(3)]. Analysis calculated for C$_{26}$H$_{27}$Cl$_3$N$_2$: C, 58.06; H, 5.06; Cl, 19.78; N, 5.21. Found: C, 58.16; H, 5.20; Cl, 19.65; N, 5.16.

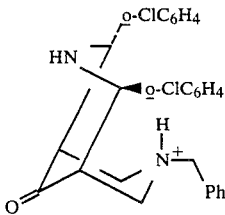

(71)

EXAMPLE XXXIII endo,endo-7-Benzyl-2,4-bis(2-chlorophenyl)-3,7-diazabicyclo[3.3.1]nonane Hydroperchlorate (72)

In a one-necked, 100-mL, round-bottomed flask, a solution of endo,endo-7-benzyl-2,4-bis(2-chlorophenyl)-3,7-diazabicyclo[3.3.1]nonane (0.4957 g, 1.14 mmol) in $C_6H_6$ (20 mL) was treated dropwise over 15 minutes with $HClO_4$ (60%, 0.5 mL) with vigorous stirring. This resulted in the precipitation of a white solid. The flask was fitted with a condenser and heated on a steam bath for an additional 5 minutes, followed by cooling to room temperature. The solution was filtered and the cloudy filtrate set aside. Recrystallization of this solid ($CH_3OH$, 30 mL) afforded the monoperchlorate endo,endo-7-benzyl-2,4-bis(2-chlorophenyl)-3,7-diazabicyclo[3.3.1]nonane hydroperchlorate (0.1050 g) as white crystals, mp 264.0°–264.5° C. (dec). The cloudy benzene filtrate was evaporated to about 2 mL, and the resulting oil was dissolved in hot $CH_3OH$ (30 mL). Upon cooling to RT, additional salt precipitated as a white powder which was filtered and recrystallized ($CH_3OH$, 65 mL) to afford additional endo,endo-7-benzyl-2,4-bis(2-chlorophenyl)-3,7-diazabicyclo[3.3.1]nonane hydroperchlorate (0.3575 g, 74% total) as white crystals, mp 260°–262° C. (dec). The spectroscopic data were as follows: IR (KBr) $cm^{-1}$ 3300 (N—H), 2850-2700 (N+—H), 1090 (Cl—O); $^1H$ NMR (DMSO-$d_6$) δ2.19 [d, J=12 Hz, 1 H, H(9)], 2.35 [d, =12 Hz, 1 H, H(9)], 2.38 [br s, 2 H, H(1,5)], 3.02 [br s, 4 H, H(6,8)ax and eq], 4.08 [br s, 2 H, $ArCH_2$], 4.88 [br s, 2 H, H(2,4), 5.63 [br s, 1 H, N—H], 7.36–7.72 [m, 13, ArH], 10.14 [br s, 1 H, N+—H]; $^{13}C$ NMR (DMSO-$d_6$) ppm 29.77 [d, C(1,5)], 31.39 [t, C(9)], 52.97 [t, C(6,8)], 60.30 [t, $ArCH_2$], 60.84 [d, C(2,4)], 127.33, 127.40, 128.92, 129.26, 129.89, 130.83, 131.18, 131.33, 136.33, 142.05, [ArC]; $^{15}N$ NMR (DMSO-$d_6$) ppm 50.05 [N(7)], 52.56 [N(3)]. Analysis calculated for $C_{26}H_{27}Cl_3N_2O_4$: C, 58.05; H, 5.07; Cl, 19.73; N, 5.21. Found: C, 58.07; H, 5.08; Cl, 19.66; N, 5.27.

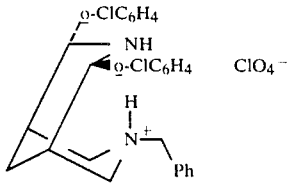

(72)

EXAMPLE XXXIV 3,6-Dibenzylhexahydro-8a-methoxy-5H-4a,8-(methanothiomethano)-2H-pyrido[3,4-e]1,3-oxazine and 2,4,10,12-Tetrabenzyl-2,4,10,12-tetraaza-15-thia-dispiro[5.1.5.3]hexadecan-7-one (73),(74)

A three-necked, 50-mL, round-bottomed flask was fitted with a condenser, an $N_2$ inlet, a magnetic stirrer, and a heating mantle. This flask was charged with paraformaldehyde (1.20 g, 40.0 mmol), benzylamine (1.07 g, 10.0 mmol), glacial acetic acid (0.66 g, 11.0 mmol), and methanol (20 mL). The apparatus was flushed with $N_2$ and the mixture boiled at reflux with stirring for 15 minutes. To the mixture was added in one portion a solution of 4-thianone (0.58 g, 5.0 mmol) in methanol (10 mL) and the resulting mixture was heated at reflux for 9 hours during which the paraformaldehyde slowly dissolved and the solution turned yellow. The solution was then cooled to room temperature and allowed to stir an additional 10 hours. Evaporation afforded a yellow oil which was partitioned between ethyl ether (50 mL) and water (50 mL). The layers were separated and the pale yellow ether layer was allowed to stand for 24 hours at −10° C. A white crystalline solid precipitated from this ethereal solution. This was filtered and set aside. The filtrate was concentrated (aspirator) to half of the previous volume and allowed to stand for 3 hours. A second crop of the white solid was precipitated which was filtered, combined with the first crop, and recrystallized (95% ethanol, 30 mL) to afford 3,6-dibenzylhexahydro-8a-methoxy-5H-4a,8-(methanothiomethano)-2H-pyrido[3,4-e]-1,3-oxazine (0.93 g, 45%) as white needles: mp 147.2°–148.8° C.; IR (KBr) $cm^{-1}$ 3030, 2940, 2830, 1365, 1358, 1104, 1067, 740, 704; $^1H$ NMR ($DCCl_3$) δ2.08 [d, J=12 Hz, 1 H, H(5)ax], 2.13 [br s, 1 H, H(8)], 2.37 [d, J=12 Hz, 1 H, H(5)eq], 2.54 [dd, J=12, 2 Hz, 1H, H(9)ax], 2.62 [d, J=11 Hz, 1 H, $ArCH_2$], 2.74 [d, J=10 Hz, 1 H, H(4)ax], 2.95 [d, J=10 Hz, 1 H, H(4)eq], 3.22 [s, 3 H, $CH_3O$], 3.25 [d, J=1 H, H(11)eq], 3.31 [d, J=13 Hz, 1 H, H(7)ax], 3.39 [dd, J=12, 2 Hz, 1 H, H(9)eq], 3.49 [d, J=11 Hz, 1 H, $ArCH_2$], 3.50 [d, J=13 Hz, 1 H, H(7)eq], 3.55 [d, J=13 Hz, 2 H, $ArCH_2$], 4.02 [d, J=8 Hz, 1 H, H(2)ax], 4.18 [d, J=8 Hz 1 H, H(2)eq], 7.22–7.38 [m, 8 H, ArH], 7.58 [d, J=8 Hz, 2 H, ArH]; $^{13}C$ NMR ($DCCl_3$) ppm 30.09 [t, C(9)], 33.42 [d, C(8)], 34.56 [t, C(11)], 37.40 [s, C(4a)], 46.27 [q, $CH_3O$], 55.38 [t, C(4)], 55.79 [t, C(5)], 57.32 [t, C(7)], 59.94 [t, $ArCH_2$], 62.59 [t, $ArCH_2$], 78.72 [t, C(2)], 96.93 [s, C(8a)], 126.48 [d, p-ArC], 127.10 [d, p-ArC], 128.15, 128.30, 128.33, 128.53 [o- and m-ArC], 137.49 [s, i-ArC], 139.66 [s, i-ArC]; $^{15}N$ NMR ($DCCl_3$) ppm 46.42 [N(3)], 35.92 [N(3)].

In a separate experiment under slightly different conditions a second product was also isolated. A three necked, 50 mL, round-bottomed flask was fitted with a dropping addition funnel, a condenser with an $N_2$ inlet, a heating mantle, a magnetic stirrer, and a stopper on the third neck. The flask was charged with a slurry of paraformaldehyde (1.20 g, 40.0 mmol) in methanol (20 mL) and was heated at reflux under $N_2$ with stirring (magnetic) for 15 minutes. To this boiling mixture was added dropwise over 3.5 hours a solution of 4-thianone (0.58 g, 5.0 mmol), benzylamine (1.07 g, 10.0 mmol), glacial acetic acid (0.66 g, 11.0 mmol) in methanol (10 mL). During the addition the paraformaldehyde slowly dissolved and the solution turned to an orange-red color. The solution was heated at reflux for an additional 3.5 hours, and then allowed to stir at room temperature for 48 hours. A white solid precipitated from the now pink solution. This solid was filtered, washed with methanol (5 mL) and recrystallized (2-propanol, 30 mL) to afford 2,4,10,12-tetrabenzyl-2,4,10,12-tetraaza-15-thia-dispiro[5.1.5.3]hexadecan-7-one (0.261 g, 8.5% relative to the amount of benzylamine used) as white needles: mp 172.5°–173.5° C.; IR (KBr) $cm^{-1}$ 3065, 3030, 2950, 2920, 2895, 2830, 2800, 1680 (C=O), 1500, 1457, 1097, 748, 736, 703; $^1$H NMR (DCCl$_3$) δ2.17 [d, J=10.8 Hz, 4 H, H(1,5,9,13)ax], 2.50 [d, J=8.8 Hz, 2 H, H(3,11)ax], 2.77 [d, J=10.8 Hz, 4 H, H(1,5,9,13)eq], 3.15 [s, 4 H, H(14,16)], 3.33 [d, J=13.0 Hz, 4 H, ArCH$_2$], 3.49 [d, J=13.0 Hz, 4 H, ArCH], 3.62 [d, J=8.8 Hz, 2 H, H(3,11)], 7.20–7.30 [m, 20 H, ArH]; $^{13}$C NMR (DCCl$_3$) ppm 36.43 [t, C(14,16)], 51.26 [s, C(6,8)], 57.63 [t, C(1,5,9,13)], 59.57 [t, ArCH$_2$], 76.58 [t, C(3,11)], 127.06 [d, p-ArC], 128.19 [d, o- or m-ArC], 128.55 [d, m- or o-ArC], 137.77 [s, i-ArC], 211.73 [s, C(7)]; $^{15}$N NMR (DCCl$_3$) ppm 43.06 [N(2,4,10,12)].

The reaction mixture filtrate was evaporated (aspirator) to an orange-red oil which was partitioned between ether (50 mL) and water (50 mL). The ether layer was treated as before to afford after recrystallization (ethanol, 25 mL) 3,6-Dibenzylhexahydro-8a-methoxy-5H-4a,8-(methanothiomethano)-2H-pyrido-[3,4-e]1,3-oxazine (0.212 g, 11%), mp 146.5°–148.0° C.; the $^{13}$C NMR spectrum of which was identical to that given previously. The pink aqueous suspension was made alkaline by the addition of NaOH pellets (0.50 g, 12.5 mmol) to give a yellow suspension. This suspension was extracted with ether (4×50 mL) and the combined ether extracts were dried (Na$_2$SO$_4$, overnight). The dry ethereal solution was filtered and evaporated (aspirator) and the resulting yellow oil was digested in boiling Skelly B (200 mL) for 30 minutes. The hot supernatant was decanted from the brown residue and evaporated (aspirator followed by vaccuum pump) to leave a pale yellow oil. The $^{13}$C NMR (DCCl$_3$) of this oil indicated that is was mostly N-benzyl-3-thia-7-azabicyclo[3.3.1]nonan-9-one (0.59 g, approximately with a small amount of 3,6-Dibenzylhexahydro-8a-methoxy-5H-4a,8-(methanothiomethano)-2H-pyrido[3,4-e]-1,3-oxazine present as an impurity. Analysis calculated for 3,6-dibenzylhexahydro-8a-methoxy-5H-4a,8-(methanothiomethano)-2H-pyrido-[3,4-e]-1,3-oxazine C$_{24}$H$_{30}$N$_2$O$_2$S: C, 70.21; H, 7.37; N, 6.82; S, 7.81. Found: C, 69.99; H, 7.51; N, 6.64; S, 7.97. Analysis calculated for 2,4,10,12-tetrabenzyl-2,4,10,12-tetraaza-15-thiadispiro[5.1.5.3]hexadecan-7-one C$_{39}$H$_{44}$N$_4$SO: C, 75.94; H, 7.19; N, 9.08; S, 5.20. Found: C, 75.73; H, 7.33; N, 9.10; S, 5.20.

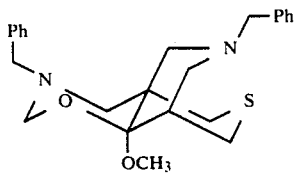

(73)

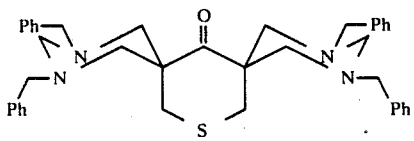

(74)

EXAMPLE XXXV 3,6-Dibenzylhexahydro-8a-methoxy-5H-4a,8-(methanoselenomethano)-2H-pyrido[3,4-e]-1,3-oxazine and 2,4,10,12-tetrabenzyl-2,4,10,12-tetraaza-15-selenadispiro[5.1.5.3]hexadecan-7-one (75),(76)

A three-necked, 50-mL, round-bottomed flask was equipped with a condenser, an N$_2$ inlet, a heating mantle, and a magnetic stirrer. The flask was charged with benzylamine (0.67 g, 6.2 mmol), glacial acetic acid (0.38 g, 6.3 mmol), paraformaldehyde (1.50 g, 50.0 mmol), and methanol (30 mL). The apparatus was flushed with N$_2$ and the mixture was heated to reflux with stirring. After 0.5 hours, the mixture was cooled to room temperature and 4-selenanone [0.75 g, 4.6 mmol] was added in one portion. The mixture was again heated at reflux for 5 hours during which all solids dissolved and the resulting solution turned yellow. The solution was then cooled to room temperature and allowed to stir overnight. The solvent was evaporated (aspirator) to leave a yellow oil which was partitioned between water (50 mL) and ether (50 mL). The layers were separated and the ether layer was allowed to stand for two days at room temperature during which a white solid precipitate formed in this solution. This was filtered and recrystallized (95% ethanol, 25 mL) to afford 3,6-dibenzylhexahydro-8a-methoxy-5H-4a,8-(methanoselenomethano)-2H-pyrido[3,4-e]-1,3-oxazine (0.250 g) as white needles: mp 160.0°–160.5° C.

The aqueous layer was cooled (ice bath) and was made alkaline by the addition of KOH pellets (85%, 1.20 g, 21.4 mmol). The resulting suspension was extracted (ether, 5×40 mL) and the combined extracts were dried (K$_2$CO$_3$, overnight). Filtration, followed by evaporation (aspirator), afforded a yellow oil which was digested in hexanes (50 mL) for 0.5 hours on a steam bath. The hot supernatant was decanted and evaporated to give another yellow oil. This was dissolved in hot 96% ethanol (10 mL) which, upon cooling, precipitated additional 3,6-dibenzylhexahydro-8a-methoxy-5H-4a,8-(methanoselenomethano)-2H-pyrido[3,4-e]-1,3-oxazine (67.0 mg, total: 0.317 g, 22%) mp 159°–160° C.

The spectroscopic data for 3,6-dibenzylhexahydro-8a-methoxy-5H-4a,8-(methanoselenomethano)-2H-pyrido[3,4-e]-1,3-oxazine were: IR (KBr) cm$^{-1}$ 2840, 1370, 1362, 1108, 1062, 1055, 762, 706; $^1$H NMR (DCCl$_3$) δ2.09 [br s, 1 H, H(8)], 2.11 [d, J=11 Hz, 1 H, H(5)ax], 2.13 [d, J=12 Hz, 1 H, H(11)ax], 2.37 [d, J=11 Hz, 1 H, H(5)eq], 2.53 [d, J=11 Hz, 1 H, H(9)ax], 2.53 [d, J=11 Hz, 1 H, ArCH$_2$], 2.72 [d, J=11 Hz, 1 H, H(4)ax], 2.93 [d, J=11 Hz, 1 H, H(4)eq], 3.25 [s, 3 H, CH$_3$O], 3.29 [d, J=12 Hz, 1 H, H(11)eq], 3.29 [d, J=14 Hz, 1 H, H(7)ax], 3.44 [d, J=11 Hz, 1 H, ArCH$_2$], 3.47 [d, J=11 Hz, 1 H, H(9)eq], 3.51 [d, J=14 Hz, 1 H, H(7)eq], 3.53 [d, J=4 Hz, 2 H, ArCH$_2$], 3.97 [d, J=8 Hz, 1 H, H(2)ax], 4.21 [d, J=8 Hz, 1 H, H(2)ax], 7.26–7.64 [m, 10 H, ArH]; $^{13}$C NMR (DCCl$_3$) ppm 20.11 [t, C(9)], 25.13 [t, C(11)], 33.22 [d, C(8)], 36.84 [s, C(4a)], 46.51 [q, CH$_3$O], 56.13 [t, C(4)], 56.67 [t, C(5)], 57.26 [t, C(7)], 60.55 [t, ArCH$_2$], 62.63 [t, ArCH$_2$], 78.76 [t, C(2)], 97.68 [s, C(8a)], 126.47 (d), 127.09 (d), 128.11 (d), 128.27 (d), 128.47 (d), 128.52 (d), 137.43 (s), 139.57 (s) [ArC]; $^{15}$N NMR (DCCl$_3$) ppm 36.20 [N(12)], 47.00 [N(3)]; $^{77}$Se NMR ppm 126.55 [Se(8)].

In a separate experiment two other products were also isolated. A three-necked, 50 mL, round-bottomed flask was fitted with a condenser, an N$_2$ inlet, a heating mantle, a magnetic stirrer, and two stoppers. The flask was charged with a solution of benzylamine (1.07 g, 10.0 mmol), glacial acetic acid (0.62 g, 10.3 mmol), paraformaldehyde (1.20 g, 40.0 mmol), and methanol (25 mL). The apparatus was flushed with N$_2$ and the mixture heated at reflux with stirring for 15 min. 4-Selenanone (0.83 g, 5.0 mmol) was then added in one postion and the mixture heated at reflux for 5 hours. The supernatant turned yellow upon addition of 4- selenanone. With continued heating, the paraformaldehyde slowly dissolved and the solution turned to a pink color. After about 3 hours, the formation of a white precipitate was noted. The reaction mixture was cooled to room temperature and stirred an additional 13 hours. The white solid was filtered from the reaction mixture, washed with methanol (5 mL) and recrystallized (95% 2-propanol, 20 mL) to give 2,4,10,12-tetrabenzyl-2,4,10,12-tetraaza-15-selenadispiro[5.1.5.3]hexadecan-7-one (57.6 mg, 1.9%) as white crystals: mp 165°–166° C.; IR (KBr) cm$^{-1}$ 3062, 3032, 2910, 2820, 2792, 1675, 1494, 1453, 1086, 1068, 741, 729, 697; $^1$H NMR (DCCl$_3$) δ2.27 [d, J=11.2 Hz, 4 H, H(1,5,9,13)ax], 2.55 [d, J=8.1 Hz, 2 H, H(3,11)ax], 2.77 [d, J=11.2 Hz, 4 H, H(1,5,9,13)eq], 3.17 [s, 4 H, H(14,16)], 3.34 [d, J=13.5 Hz, 4 H, ArCH$_2$], 3.50 [d, J=13.5 Hz, 4 H, ArCH$_2$], 3.54 [d, J=8.1 Hz, 2 H, H(3,11)eq], 7.20–7.30 [m, 20 H, ArH]; $^{13}$C NMR (DCCl$_3$) ppm 26.67 [t, C(14,15)], 51.12 [s, C(6,8)], 58.35 [t, C(1,5,9,13)], 59.58 [T, ArCH$_2$], 126.93 [d, p-ArC], 128.05 [d, o- or m-ArC], 128.46 [d, m- or o-ArC], 137.67 [s, i-ArC], 211.80 [s, C(7)]; $^{15}$N NMR (DCCl$_3$) ppm 43.57.

The reaction mixture filtrate was evaporated (aspirator) to leave a pink oil which was partitioned between ether (50 mL) and water (50 mL). The colorless ether layer was separated and treated as before to afford after recrystallization 3,6-dibenzylhexahydro-8a-methoxy-5H-4a,8-(methanoselenomethano)-2H-pyrido[3,4-e]-1,3-oxazine (0.2030 g, 8.8%), mp 159°–160° C., the IR and $^{13}$C NMR spectra of which were identical to that given previously. The pink aqueous suspension from the partitioning was made alkaline by the addition of KOH pellets (85%, 2.00 g, 30.3 mmol) to give an oily yellow suspension. This suspension was extracted with ether (5×40 mL) and the combined extracts dried (K$_2$CO$_3$, overnight). The ethereal extracts were then filtered and evaporated to leave an orange oil which was digested in boiling hexanes (50 mL) for 30 min. The hot supernatant was decanted and evaporated to give a yellow oil. This was dissolved in hot 95% ethanol (30 mL), decolorized with carbon, and evaporated to 10 mL. Upon standing at −10° C. for 1 day, white needles precipitated. These were filtered and air dried to afford 7-benzyl-3-selena-7-azabicyclo[3.3.1]nonan-9-one (0.38 g, 25.8%), mp 91°–92° C. Analysis calculated for 3,6-dibenzylhexahydro-8a-methoxy-5H-4a,8-(methanoselenomethano)-2H-pyrido[3,4-e]-1,3-oxazine C$_{24}$H$_{30}$N$_2$O$_2$Se: C, 63.01; H, 6.61; N, 6.12; Se, 17.26. Found: C, 62.88; H, 6.83; N, 6.02; Se, 16.91.

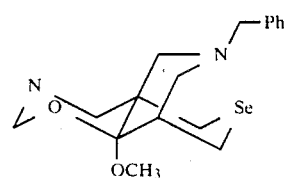

(75)

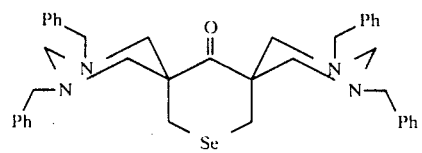

(76)

EXAMPLE XXXVI 3,6-Dibenzylhexahydro-8a-methoxy-5H-4a,8-(methanothiomethano)-2H-pyrido[3,4-e]-1,3-oxazine dihydroperchlorate (77)

A 125-mL Erlenmeyer flask was charged with a solution of ketal 3,6-dibenzylhexahydro-8a-methoxy-5H-4a,8-(methanothiomethano)-2H-pyrido[3,4-e]-1,3-oxazine (1.00 g, 2.44 mmol) in benzene (20 mL). To this solution was added dropwise over 15 min a solution of HClO$_4$ (60%, 1.00 g, 5.97 mmol) in 2-propanol (5 mL) with vigorous stirring (magnetic). This precipitated the salt as a white powdery solid. To prevent caking of the precipitate it was found necessary to add additional 2-propanol (10 mL). The mixture was stirred an additional 1 hour at room temperature. The salt was filtered, recrystallized (ethanol, 25 mL), and dried (Abderhalden, P$_2$O$_5$, 77° C., vacuum pump, 12 hours) to afford 3,6-dibenzylhexahydro-8a-methoxy-5H-4a,8-(methanothiomethano)-2H-pyrido[3,4-e]-1,3-oxazine dihydroperchlorate (0.60 g, 40%) as white crystals: mp 160°–162° C. (dec); IR(KBr) cm$^{-1}$ 2760–2845 (N+—H), 1080 (Cl—O); $^1$H NMR (DMSO-d$_6$) δ2.17 [d, J=11.7 Hz, 1 H, H(4)ax], 2.35 [d, J=11.7 Hz, 1 H, H(4)eq], 2.43 [d, J=13.0 Hz, 1 H, H(11)ax], 2.64 [br s, 1 H, H(8)], 2.76 [d, J=13.6 Hz, 1 H, H(9)ax], 3.00 [d, J=13.0 Hz, H(11)eq], 3.18 [s, 3 H, CH$_3$O], 3.22 [m, 2H, H(9)eq and ArCH$_2$], 3.32 [d, J=13.6 Hz, 1 H, H(5)ax], 3.46 [d, J=12.0 Hz, H(7)ax], 3.57 [d, J=13.6 Hz, 1 H, H(5)eq], 3.79 [d, J=12.0 Hz, H(7)eq], 4.00 [d, J=7.3 Hz, 1 H, H(2)ax], 4.19 [d, J=12.0 Hz, 1 H ArCH$_2$], 4.24 [d, J=7.3 Hz, 1 H, H(2)eq], 4.40 [dd, J=12.6, 5.9 Hz, ArCH$_2$], 4.54 [dd, J=12.6, 3.9 Hz, 1 H, ArCH$_2$], 7.25–7.39 [m, 5 H, ArH], 7.49–7.64 [m, 5 H, ArH], 9.53 [br s, 1 H, N+—H]; $^{13}$C NMR (DMSO-d$_6$) ppm 28.26 [t, C(9)], 31.34 [d, C(8)], 31.80 [t, C(11)], 37.39 [s, C(4a)], 46.36 [q, CH$_3$O], 52.33 [T, C(4)], 54.25 [t, C(7)], 55.40 [t, C(5)], 56.21 [t, ArCH$_2$], 60.20 [t, ArCH$_2$], 78.00 [t, C(2)], 93.75 [s, C(8a)], 127.14, 128.27, 129.09, 129.65, 130.60, 136.98 [ArC]. Analysis calculated for C$_{24}$H$_{30}$N$_2$N$_2$O$_2$S.2 HClO$_4$: C, 47.14; H, 5.27; Cl, 11.59; N, 4.58; S, 5.24. Found: C, 47.22; H, 5.14; Cl, 11.38; N, 4.44; S, 5.47.

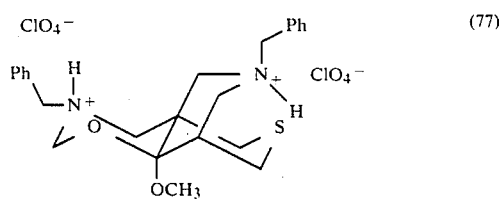

(77)

In order to illustrate the useful biological activity of the compounds according to the present invention, selected derivatives were tested using dog models for antiarrhythmic activity. The clinically used drug lidocaine was employed as a basis for comparison. In the dog model an infarction was created in a small area of the heart and thereafter an electrical pacing was administered to generate a sustained ventricular tachycardia (VT). This irregular bearing pattern of the heart results in a reduction of the heart's pumping capacity in a manner now accepted as resembling symptoms observed in humans during heart attack (see: Scherlag, B. J. et al., Am. J. Cardiol. 1983, 51, 207; Bailey, B. B. et al, J. Med. Chem., 1984, 27, 759; and U.S. Pat. No. 4,581,361 for further details, said references incorporated herein for such purposes). The effects of the selected compounds in terms of ability to reduce the rate of the ventricular tachycardia or to eliminate the same (i.e., to not allow VT to be sustained) is then evaluated and compared to the drug lidocaine. The following Table contains the data observed as result of the testing.

TABLE

Antiaarhythmic Data for Representative Compounds of the 3,7-Diheterabicyclo[3.3.1]nonanes and Derivatives

| Compound | Pacing Rate* | Rate of MBP$^a$ | Rate of SVT$^b$ | 3 mg/kg$^c$ Rate of MBP | 3 mg/kg$^c$ Rate of SVT | 6 mg/kg$^d$ Rate of MBP | 6 mg/kg$^d$ Rate of SVT |
|---|---|---|---|---|---|---|---|
| | 450(C)$^e$ | 170$^g$ (50)$^h$ | 450 | | | | |
| (45) | 450(L)$^f$ 450 | | | 100$^i$ | 375 330 | | |
| | 330(C) | 160$^g$ (70)$^h$ | 330 | | | | |
| (47) | 330 | | | | 240 | | 270(NS) |
| | 330(C) | 160$^g$ (70)$^h$ | 330 | | | | |
| (50) | 330 | | | 85 | 300 | 70 | 310 |
| | 330(C) | 70$^h$ | 270 | | | | |
| | 390(L) | | | | 270(NS) | | |
| | 360(L) | | | | | | 240 |
| (66) | 360 | | | 95 | 330(NS) | | |
| (66) | 390 | | | | | 95 | 240 |
| | 360(C) | 90$^h$ | 390 | | | | |
| | 330(L) | | | | 300 | | |
| | 300(L) | | | | | | 270 |
| (66) | 390 | | | 99 | (NS) | | |
| | 390(C) | 90$^h$ | 390 | | | | |
| | 390(L) | | | | 300 | | |
| | 390(L) | | | | 300 | | 270 |
| (65) | 390 | | | 92 | 210 | | |
| (65) | 390 | | | | | 85 | (NS) |
| | 390(C) | 102$^h$ | 390 | | | | |
| | 390(L) | | | | 330 | | |
| | 390(L) | | | | | | 210 |
| (28) | 390 | | | 99 | 330 | | |
| | 390(C) | 70$^h$ | 390 | | | | |
| | 360(L) | | | | 360 | | |
| | 360(L) | | | | | | 330 |
| (71) | 390 | | | 85 | 340 | | |
| | 360(C) | 80$^g$ | 330 | | | | |
| | 390(L) | | | | 360 | | |
| | 330(L) | | | | | | 210 |
| (72) | 360 | | | 90 | 330 | | |
| (72) | 390 | | | | | 86 | 330 |
| | 330(C) | 70$^h$ | 330 | | | | |
| (59**) | 330 | | | 70 | 300 | | |
| (59**) | 330 | | | | | 75 | 280 |
| | 390(C) | 95$^h$ | (NS) | | | | |
| | 390(L) | | | | No VT | | |
| | 360(L) | | | | | | 270 |
| (77) | 390 | | | 98 | 330 | | |
| (77) | 390 | | | | | 101 | 330 |

$^a$Mean Blood Pressure during normal sinus rhythm before a VT is induced.
$^b$Sustained Ventricular tachycardia
$^c$3 mg of compound per kg of dog model
$^d$6 mg of compound per kg of dog model
$^e$(C) Control before compound is added to dog model
$^f$(L) Lidocaine
$^g$MBP before compound is added to dog model
$^h$MBP during sustained VT
$^i$MBP during sustained VT
$^j$(NS) Nonsustained VT
*Electrically stimupacing rate required to induce an SVT
endo-exo isomer From the Table, it is concluded that the compound (45) was extremely effective in reducing the ventricular tachycardia (as compared to lidocaine) at a concentration of only 3 mg/kg. The same was true in compounds (28),(50), (59),(71), and (72). In (47),(65), and (66), the VT generated in the dog model was virtually eliminated by the compound and a normal sinus rhythm was observed. Thus, the generated VT was not sustained in the presence of the compound. In contrast, the VT was sometimes reduced by the presence of lidocaine, but was rarely eliminated. Thus, the heterocycles claimed in the application appear to have electrocardiology properties equal or superior to lidocaine, a clinically used drug for the treatment of victims of heart attacks. This in combination with the possibility that the hetera atoms afford the use of a radioactive isotope for imaging (e.g., the use of $^{75}$Se) purposes creates the possibility of in vivo analysis simultaneously with therapeutic treatment.

In principle, it is felt that the compositions of the present invention can be employed by themselves, in combination with each other, or in combination with other drugs to achieve either individually or in combination the desired antiarrhythmic properties. It is envisioned that the composition can be utilized and administered in a variety of methods including by way of example, but not limited thereto, intravenously, orally, by suppository, by inhalation, and the like. Furthermore, it is generally felt that the compositions as claimed either specifically possess antiarrhythmic activity or generally are broadly biologically active or the respective compositions are intermediaries to antiarrhythmic and biologically active species that are released or created in situ as the result of the administration of the drug.

Having thus described and exemplified the preferred embodiments with a certain degree of particularity, it is to be understood that the invention is not to be limited to the embodiments set forth herein for purposes of exemplification, but is to be limited only by the scope of the attached claims, including a full range of equivalents to which each element thereof is entitled.

We claim:

1. A 3,7-diheterabicyclo[3.3.1]nonane characterized by the formula:

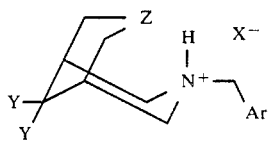

where Ar is

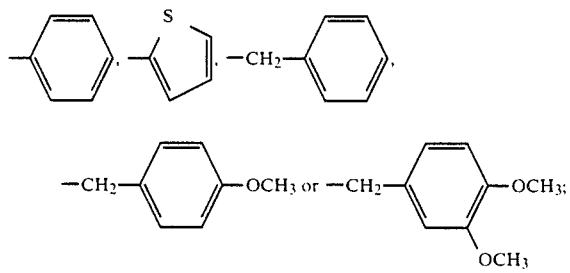

Z is Se; X⁻ is ClO₄⁻, Cl⁻, Br⁻ or I⁻; and Y is —OH or —OCH₃.

2. A 3,7-diheterabicyclo[3.3.1]nonane of claim 1 where Ar is

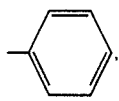

X⁻ is ClO₄⁻, and Y is —OH.

3. A 3,7-diheterabicyclo[3.3.1]nonane characterized by the formula:

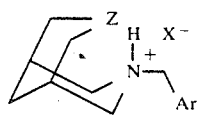

where Ar is

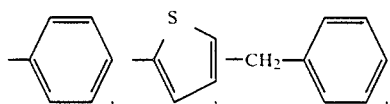

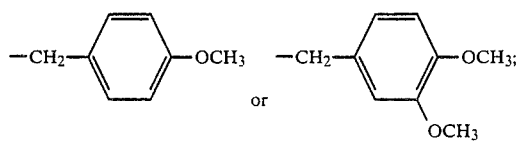

Z is Se; X⁻ is ClO₄⁻, Cl⁻, Br⁻ or I⁻.

4. A 3,7-diheterabicyclo[3.3.1]nonane of claim 3 where Ar is

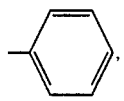

and X⁻ is ClO₄⁻.

5. A 3,7-diheterabicyclo[3.3.1]nonane of claim 3 where Ar is

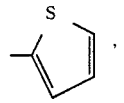

and X⁻ is ClO₄⁻.

6. A 3,7-diheterabicyclo[3.3.1]nonane of claim 3 where Ar is

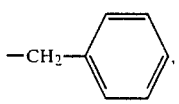

and X⁻ is ClO₄⁻.

7. A 3,7-diheterabicyclo[3.3.1]nonane of claim 3 where Ar is

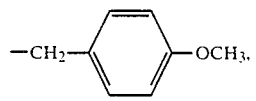

and X⁻ is ClO₄⁻.

8. A 3,7-diheterabicyclo[3.3.1]nonane of claim 3 where Ar is

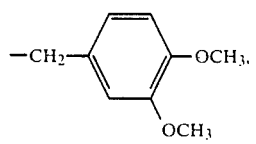

and X⁻ is ClO₄⁻.

9. A 3,7-diheterabicyclo[3.3.1]nonane characterized by the formulae:

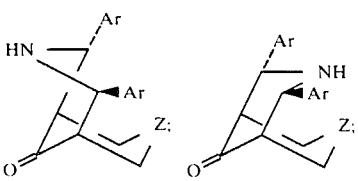

-continued

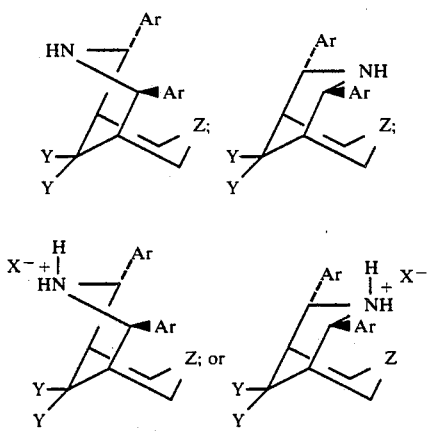

where Ar is

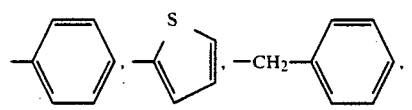

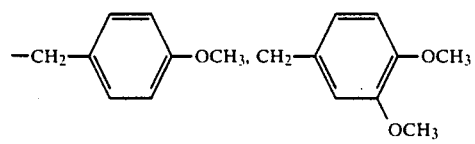

or o—ClC$_6$H$_4$ or p-ClC$_6$H$_4$; Z is Se; X$^-$ is ClO$_4$$^-$, Cl$^-$, Br$^-$ or I$^-$; and Y is —H, —OH or —OCH$_3$.

10. A 3,7-diheterabicyclo[3.3.1]nonane of claim 9 where Ar is

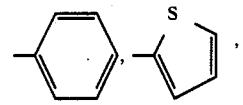

p-ClC$_6$H$_4$, or o-ClC$_6$H$_4$.

11. A 3,7-diheterabicyclo[3.3.1]nonane of claim 10 where Ar is

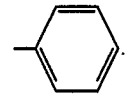

12. A 3,7-diheterabicyclo[3.3.1]nonane of claim 10 where Ar is

13. A 3,7-diheterabicyclo[3.3.1]nonane of claim 10 where Ar is p-ClC$_6$H$_4$.

14. A 3,7-diheterabicyclo[3.3.1]nonane of claim 10 where Ar is o-ClC$_6$H$_4$.

15. A 3,7-diheterabicyclo[3.3.1]nonane of claim 11 wherein the compound is an acid salt and X$^-$ is ClO$_4$$^-$.

16. A 3,7-diheterabicyclo[3.3.1]nonane of claim 12 wherein the compound is an acid salt and X$^-$ is ClO$_4$$^-$.

17. A 3,7-diheterabicyclo[3.3.1]nonane of claim 13 wherein the compound is an acid salt and X$^-$ is ClO$_4$$^-$.

18. A 3,7-diheterabicyclo[3.3.1]nonane of claim 14 wherein the compound is an acid salt and X$^-$ is ClO$_4$$^-$.

* * * * *